US012623999B2

(12) United States Patent
Takeuchi et al.

(10) Patent No.: US 12,623,999 B2
(45) Date of Patent: May 12, 2026

(54) CARBAMATE PRODUCTION METHOD, CARBAMATE ESTER PRODUCTION METHOD, AND UREA DERIVATIVE PRODUCTION METHOD

(71) Applicants: NATIONAL INSTITUTE OF ADVANCED INDUSTRIAL SCIENCE AND TECHNOLOGY, Tokyo (JP); TOSOH CORPORATION, Shunan (JP)

(72) Inventors: Katsuhiko Takeuchi, Tsukuba (JP); Kazuhiro Matsumoto, Tsukuba (JP); Norihisa Fukaya, Tsukuba (JP); Hiroki Koizumi, Tsukuba (JP); Jun-Chul Choi, Tsukuba (JP); Masahito Uchida, Ayase (JP); Seiji Matsumoto, Minato-ku (JP); Satoshi Hamura, Minato-ku (JP)

(73) Assignees: NATIONAL INSTITUTE OF ADVANCED INDUSTRIAL SCIENCE AND TECHNOLOGY, Tokyo (JP); TOSOH CORPORATION, Shunan (JP)

( * ) Notice: Subject to any disclaimer, the term of this patent is extended or adjusted under 35 U.S.C. 154(b) by 735 days.

(21) Appl. No.: 18/000,646

(22) PCT Filed: Jun. 3, 2021

(86) PCT No.: PCT/JP2021/021188

§ 371 (c)(1),
(2) Date: Dec. 2, 2022

(87) PCT Pub. No.: WO2021/246485

PCT Pub. Date: Dec. 9, 2021

(65) Prior Publication Data

US 2023/0212110 A1 Jul. 6, 2023

(30) Foreign Application Priority Data

| | | | |
|---|---|---|---|
| Jun. 5, 2020 | (JP) | ................................ | 2020-098388 |
| Jun. 5, 2020 | (JP) | ................................ | 2020-098490 |
| Jun. 5, 2020 | (JP) | ................................ | 2020-098497 |
| Feb. 24, 2021 | (JP) | ................................ | 2021-027268 |
| Feb. 24, 2021 | (JP) | ................................ | 2021-027277 |

(51) Int. Cl.

| | |
|---|---|
| ***C07C 269/04*** | (2006.01) |
| ***B01J 31/12*** | (2006.01) |
| ***B01J 31/22*** | (2006.01) |
| ***C07C 273/18*** | (2006.01) |
| ***C07D 233/34*** | (2006.01) |

(52) U.S. Cl.

CPC ........... *C07C 269/04* (2013.01); *B01J 31/122* (2013.01); *B01J 31/2208* (2013.01); *B01J 31/226* (2013.01); *B01J 31/2295* (2013.01); *C07C 273/1836* (2013.01); *C07D 233/34* (2013.01); *B01J 2231/4283* (2013.01); *B01J 2531/26* (2013.01); *B01J 2531/42* (2013.01); *B01J 2531/46* (2013.01); *B01J 2531/847* (2013.01)

(58) Field of Classification Search

None

See application file for complete search history.

(56) References Cited

U.S. PATENT DOCUMENTS

| | | | |
|---|---|---|---|
| 3,056,820 | A | 10/1962 | Martinek |
| 4,801,746 | A | 1/1989 | Baenens |
| 2014/0051858 | A1 | 2/2014 | Hur et al. |
| 2015/0099886 | A1 | 4/2015 | Hur et al. |
| 2018/0282265 | A1 | 10/2018 | Makhynya et al. |

FOREIGN PATENT DOCUMENTS

| | | | |
|---|---|---|---|
| CN | 1821222 | A | 8/2006 |
| JP | 62-09560 | A | 2/1987 |
| JP | 62-039560 | A | 2/1987 |
| JP | 2015-137255 | A | 7/2015 |
| JP | 2017-31046 | A | 2/2017 |
| JP | 2019-500356 | A | 1/2019 |
| WO | WO 2012/111946 | A2 | 8/2012 |
| WO | WO 2012/111946 | A3 | 8/2012 |
| WO | WO 2015/133247 | A1 | 9/2015 |

OTHER PUBLICATIONS

International Search Report mailed on Aug. 24, 2021 in PCT/JP2021/021188 filed on Jun. 3, 2021 (3 pages).

Carrera, G.V.S.M. et al., "Synthesis and properties of reversible ionic liquids using $CO_2$, mono- to multiple functionalization", Tetrahedron, 2012, vol. 68, pp. 7408-7413.

Ghodsinia, S. S. E. et al., "A high-yielding, expeditious, and multicomponent synthesis of urea and carbamate derivatives by using triphenylphosphine/trichloroisocyanuric acid system", Phosphorus, Sulfur, and Silicon and the Related Elements, 2016, vol. 191, No. 1, pp. 104-110, 8 total pages.

Peterson, S. L. et al., "Parallel Synthesis of Ureas and Carbamates from Amines and $CO_2$ under Mild Conditions", Organic Letters, 2010, vol. 12, No. 6, pp. 1340-1343.

Singh, K. N., "Mild and Convenient Synthesis of Organic Carbamates from Amines and Carbon Dioxide using Tetraethylammonium Superoxide", Synthetic Communications, 2007, vol. 37, pp. 2651-2654.

(Continued)

*Primary Examiner* — Renee Claytor
*Assistant Examiner* — Jennifer C Sawyer
(74) *Attorney, Agent, or Firm* — Oblon, McClelland, Maier & Neustadt, L.L.P.

(57) ABSTRACT

A method for producing a carbamic acid salt, including contacting a carbon dioxide-containing mixed gas having a partial pressure of carbon dioxide of 0.001 atm or more and less than 1 atm with an amino group-containing organic compound in the presence of a base in at least one organic solvent selected from the group consisting of an organic solvent having 2 or more and 8 or less carbon atoms, and a method for producing a carbamic acid ester or a urea derivative using the carbamic acid salt.

11 Claims, No Drawings

(56) References Cited

OTHER PUBLICATIONS

Chaturvedi, D. et al., "An Efficient, One-Pot Synthesis of Carbamates from the Corresponding Alcohols Using Mitsunobu's Reagent", Monatshefte für Chemie, 2007, vol. 138, pp. 57-60.
Mase, Nobuyuki et al., "Organocatalytic Knoevenagel Condensations by Means of Carbamic Acid Ammonium Salts", Organic Letters, 2013, vol. 15, No. 815(8), pp. 1854-1857.
Novotný, Michal et al., "Transkarbams as transdermal permeation enhancers: Effects of ester position and ammonium carbamate formation", Bioorganic & Medicinal Chemistry Letters, 2010, vol. 20, No. 9, pp. 2726-2728.
Hampe, Erin M. et al., "Exploring reversible reactions between $CO_2$ and amines", Tetrahedron, 2003, vol. 59, No. 48, pp. 9619-9625.
Aresta, Michele et al., "Role of the Macrocyclic Polyether in the Synthesis of N-Alkylcarbamate Esters from Primary Amines, $CO_2$ and Alkyl Halides in the Presence of Crown-Ethers", Tetrahedron, 1992, vol. 48, No. 8, pp. 1515-1530.
Takeuchi, Katsuhiko et al., "Carbon Dioxide Capture and Utilization by Chemical Processing and Bioprocessing for Break Away from Dependence on Oil", Jul. 31, 2020, pp. 165-171 (17 total pages).
Extended European Search Report dated May 6, 2024 issued in corresponding European Patent Application No. 21817120.5, 9 pages.

CARBAMATE PRODUCTION METHOD, CARBAMATE ESTER PRODUCTION METHOD, AND UREA DERIVATIVE PRODUCTION METHOD

CROSS-REFERENCE TO RELATED APPLICATIONS

The present application is a 35 U.S.C. § 371 national stage patent application of International patent application PCT/JP2021/021188, filed on Jun. 3, 2021, which is based on and claims the benefits of priority to Japanese Application No. 2020-098388, filed on Jun. 5, 2020, Japanese Application No. 2020-098490, filed on Jun. 5, 2020, Japanese Application No. 2020-098497, filed on Jun. 5, 2020, Japanese Application No. 2021-027268, filed on Feb. 24, 2021, and Japanese Application No. 2021-027277, filed on Feb. 24, 2021. The entire contents of all of the above applications are incorporated herein by reference.

TECHNICAL FIELD

The present invention relates to a method for producing a carbamic acid salt, a method for producing a carbamic acid ester, and a method for producing a urea derivative.

BACKGROUND ART

Carbamic acid salts are useful compounds having a wide range of applications for medical drugs, agricultural chemicals, various fine chemicals, and synthetic raw materials thereof. There have been heretofore studied methods for synthesizing carbamic acid salts from amines and $CO_2$.

For example, Patent Document 1 relates to a method for producing a carbamate (carbamic acid ammonium salt) from $CO_2$ in a flue gas, in which N-(2-aminoethyl)carbamate is obtained as a white crystal by introducing (bubbling) an exhaust gas having a content of $CO_2$ of 5 to 21% by volume, into a 0.75 to 1.00 mol/L ethylenediamine/methanol solution under ice bath conditions at 0° C.±1° C., and separating, washing, and purifying a reaction product.

Patent Document 2 discloses a method for producing a carbamic acid derivative powder, which is a method for obtaining various ammonium carbamates as solids by reacting carbon dioxide and various liquid amines such as ethylenediamine and benzylamine in solvents under conditions of a temperature range from −30 to 500° C. and a pressure range from 0.3 to 100 MPa.

Patent Document 3 relates to an absorber and a generator of air-derived carbon dioxide, and discloses a method for absorbing carbon dioxide in the air by leaving a specific alkylamine substituted with a hydroxy group or an amino group which may be substituted, in an air atmosphere.

Non-Patent Document 1 reports a synthesis of ammonium carbamate which is a novel carbamic acid-based ionic liquid by reacting various primary to tertiary amines in solvents in the presence of an organic super strong base such as diazabicycloundecene (DBU (registered trademark)), tetramethylguanidine (TMG) and/or the like under a carbon dioxide atmosphere at a temperature ranging from room temperature to 40° C. and a pressure of 5 to 60 bar, as well as studies about the reaction conditions.

Carbamic acid esters are known as derivatives of carbamic acid salts. Carbamic acid esters are useful compounds having a wide range of applications for medical drugs, agricultural chemicals, various fine chemicals, and synthetic raw materials thereof. There have been heretofore proposed methods for producing carbamic acid esters by use of carbon dioxide at ordinary pressure.

For example, Non-Patent Document 2 studies as a method for synthesizing a carbamate derivative, a multicomponent synthesis using ammonium carbamate synthesized in situ from a reaction of amine and $CO_2$, as a carbonyl source, a stoichiometric amount of triphenylphosphine, and a stoichiometric amount of trichloroisocyanuric acid (TCCA). In Non-Patent Document 2, a $CO_2$ gas at 1 atm is used and a non-renewable sacrificial reagent is used.

Non-Patent Document 3 reports a method for synthesizing a carbamic acid ester via a carbamic acid by use of a $CO_2$ gas at 1 atm and 1,8-diazabicyclo[5.4.0]undec-7-ene as a catalyst. In Non-Patent Document 3, $PBu_3$ and DBAD (di-tert-butyl azodicarboxylate) as non-renewable sacrificial reagents are used.

Non-Patent Document 4 reports a synthesis of a carbamic acid ester from amine and a $CO_2$ gas by use of $KO_2/Et_4NBr$ or the like as a non-renewable sacrificial reagent.

Non-Patent Document 5 reports a synthesis of a carbamic acid ester via a carbamic acid according to the Mitsunobu reaction by use of a $CO_2$ gas at 1 atm and $Ph_3P$ and DEAD (diethyl azodicarboxylate) as sacrificial reagents.

Urea derivatives are known as analogs of carbamic acid salts. Urea derivatives are useful compounds having a wide range of applications for medical drugs, agricultural chemicals, various fine chemicals, and synthetic raw materials thereof. For example, 1,3-dimethyl-2-imidazolidinone, N,N'-dimethylpropylene urea, and the like as aprotic polar solvents can be used as alternative solvents for carcinogenic HMPA (hexamethylphosphoric triamide). Ethylene urea is used in woven finishing materials, paints, and the like. For example, urea derivatives having the following structure, as anti-HIV agents, are reported as basic skeletons of pharmaceutical products.

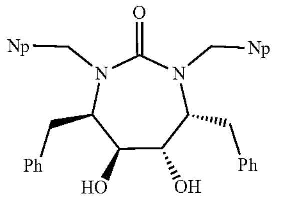

Urea derivatives have been conventionally produced industrially by reacting amines and ureas or phosgenes. However, use of ureas causes the occurrence of ammonium salts as by-products. In addition, alternative methods to synthesis methods using phosgenes are demanded from the viewpoint of handling. In this regard, there is studied as a method for synthesizing a urea derivative, a multicomponent synthesis using ammonium carbamate synthesized in situ from a reaction of amine and $CO_2$, as a carbonyl source, a stoichiometric amount of triphenylphosphine, and a stoichiometric amount of trichloroisocyanuric acid (TCCA) (see Non-Patent Document 2.).

PRIOR ART DOCUMENT

Patent Document

Patent Document 1: Chinese Patent Application Publication No. 1821222
Patent Document 2: International Publication No. WO 2012/111946
Patent Document 3: Japanese Patent Application Publication No. 2017-031046

Non-Patent Document

Non-Patent Document 1: Tetrahedron, (Holland), 2012, vol. 68, p. 7408-7413
Non-Patent Document 2: S. S. E. Ghodsinia, B. Akhlaghinia, Phosphorus Sulfur Silicon Relat. Elem., 2016, vol. 191, p. 1-7
Non-Patent Document 3: Scott L. Peterson, Sabrina M. Stucka, Christopher J. Dinsmore, Org. Lett. 2010, 12, p. 1340-1343
Non-Patent Document 4: KrishnaNand Singh, Synth. Commun. 2007, 37, p. 2651-2654
Non-Patent Document 5: Devdutt Chaturvedi, Nisha Mishura, Virendra Mishra, Monats. Chem. 2007, 138, p. 57-60

SUMMARY OF THE INVENTION

Problems to be Solved by the Invention

A first object of the present invention is to provide a novel method for producing a carbamic acid salt from carbon dioxide at a partial pressure lower than an ordinary pressure.

All the carbamic acid ester production methods of Non-Patent Documents 2 to 5 need either sacrificial reagents or alkyl halides which are poorly environmentally friendly.

A second object of the present invention is to provide a method for producing a carbamic acid ester with a carbamic acid salt as a raw material, with neither any sacrificial reagent, nor any alkyl halide.

A third object of the present invention is to provide a method for producing a urea derivative with a carbamic acid salt as a raw material by a catalyst reaction with no need for any sacrificial reagent.

Means for Solving the Problems

The present inventors have made intensive studies in order to achieve the first object, and as a result, have found that a carbamic acid salt is efficiently produced by contacting a carbon dioxide-containing mixed gas and an amino group-containing organic compound in the presence of a base in a solvent and thus have completed a first aspect of the present invention.

The first aspect of the present invention provides the following specific embodiments and the like.

[A1] A method for producing a carbamic acid salt, comprising contacting a carbon dioxide-containing mixed gas having a partial pressure of carbon dioxide of 0.001 atm or more and less than 1 atm with an amino group-containing organic compound in the presence of a base in at least one organic solvent selected from the group consisting of an organic solvent having 2 or more and 8 or less carbon atoms.

[A2] The method for producing a carbamic acid salt according to [A1], wherein the method is a method for producing a compound represented by the following general formula (a) or a compound represented by the following general formula (b):

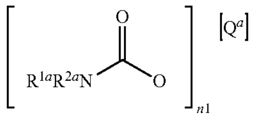

(a)

in the formula (a), $R^{1a}$ represents a hydrogen atom, an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom; $R^{2a}$ represents an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom; $Q^a$ represents an n1-valent counter cation derived from the base, and is an ammonium cation, an amidinium cation, a guanidinium cation, a phosphonium cation, a phosphazenium cation, a carbocation, an alkali metal cation, or an alkaline earth metal cation; and n1 is 1 or 2;

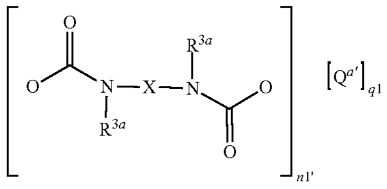

(b)

in the formula (b), $R^{3a}$ each independently represents a hydrogen atom, an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom; X represents a divalent hydrocarbon group which may contain an oxygen atom and/or a nitrogen atom; $Q^{a'}$ represents an n1'-valent counter cation derived from the base, and is an ammonium cation, an amidinium cation, a guanidinium cation, a phosphonium cation, a phosphazenium cation, a carbocation, an alkali metal cation, or an alkaline earth metal cation; n1' is 1 or 2; and q1 is 2 when n1' is 1, and q1 is 1 when n1' is 2.

[A3] The method for producing a carbamic acid salt according to [A1] or [A2], wherein the amino group-containing organic compound is an amino group-containing organic compound represented by the following general formula (B) or an amino group-containing organic compound represented by the following general formula (C):

$$R^{11a}R^{21a}NH \quad (B)$$

in the formula (B), $R^{11a}$ represents a hydrogen atom, an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom; and $R^{21a}$ represents an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom;

(C)

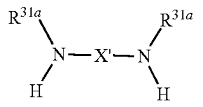

in the formula (C), $R^{31a}$ each independently represents a hydrogen atom, an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom; and X' represents a divalent hydrocarbon group which may contain an oxygen atom and/or a nitrogen atom.

[A4] The method for producing a carbamic acid salt according to any of [A1] to [A3], wherein the base is at least one selected from the group consisting of an organic base, an alkali metal salt, and an alkaline earth metal salt.

[A5] The method for producing a carbamic acid salt according to any of [A1] to [A4], wherein a concentration of the amino group-containing organic compound in the solvent is 0.01 mol/L or more and 10.00 mol/L or less.

[A6] The method for producing a carbamic acid salt according to any of [A1] to [A5], wherein the partial pressure of carbon dioxide in the carbon dioxide-containing mixed gas is 0.1 atm or more and 0.5 atm or less.

The present inventors have made intensive studies in order to achieve the second object, and as a result, have found that a carbamic acid ester is generated from a carbamic acid salt and a metal alkoxide and thus have completed a second aspect of the present invention.

The second aspect of the present invention provides the following specific embodiments and the like.

[B1] A method for producing a carbamic acid ester, comprising a reaction step of producing a carbamic acid ester having a structure represented by the following formula (a-1) or (a-2), from a carbamic acid salt and a metal alkoxide:

(a-1)

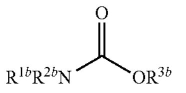

(a-2)

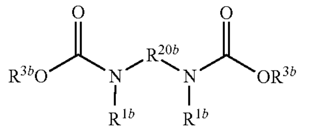

in the formulae, $R^{1b}$ each independently represents a hydrogen atom, or an unsubstituted or a substituted monovalent hydrocarbon group, $R^{2b}$ and $R^{3b}$ each independently represents an unsubstituted or a substituted monovalent hydrocarbon group, and $R^{20b}$ represents an unsubstituted or a substituted divalent hydrocarbon group.

[B2] The method for producing a carbamic acid ester according to [B1], wherein the carbamic acid salt is a carbamic acid salt represented by formula (B-1), the metal alkoxide is a metal alkoxide represented by formula (C-1), and the carbamic acid ester having the structure represented by the formula (a-1) is a carbamic acid ester represented by formula (A-1):

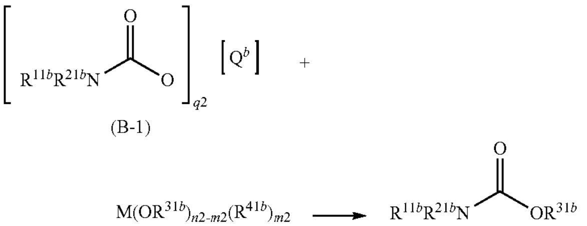

(B-1) (C-1) (A-1)

in the formulae, $R^{11b}$ represents a hydrogen atom, or an unsubstituted or a substituted monovalent hydrocarbon group; $R^{21b}$ and $R^{31b}$ each independently represents an unsubstituted or a substituted monovalent hydrocarbon group; $R^{41b}$ each independently represents an unsubstituted or a substituted hydrocarbon ligand, an unsubstituted or a substituted alkoxy ligands, amide ligands, and halide ligands different from $—OR^{31b}$; M represents a metal atom or a semimetal atom; n2 represents the oxidation number of M and (n2-m2) is an integer of 1 to 6; m2 represents an integer of 0 or more and (n2-1) or less; $Q^b$ represents a q2-valent counter cation; and q2 is 1 or 2.

[B3] The method for producing a carbamic acid ester according to [B2], wherein $Q^b$ is a cation selected from the group consisting of an ammonium cation, an amidinium cation, a guanidinium cation, a phosphonium cation, a phosphazenium cation, a carbocation, an alkali metal cation, and an alkaline earth metal cation.

[B4] The method for producing a carbamic acid ester according to [B1], wherein the carbamic acid salt is a carbamic acid salt represented by formula (B-2), the metal alkoxide is a metal alkoxide represented by formula (C-2), and the carbamic acid ester having the structure represented by the formula (a-2) is a carbamic acid ester represented by formula (A-2):

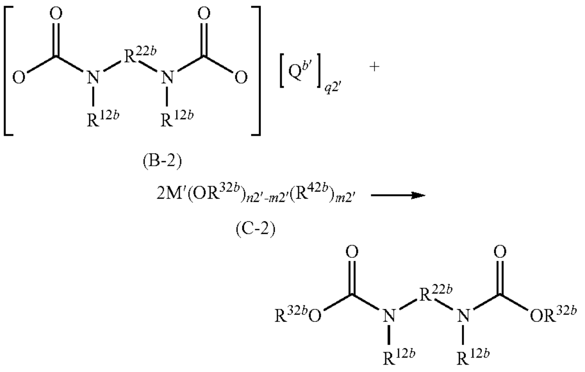

(B-2) (C-2) (A-2)

in the formulae, $R^{12b}$ each independently represents a hydrogen atom, or an unsubstituted or a substituted monovalent hydrocarbon group; $R^{22b}$ represents an unsubstituted or a substituted divalent hydrocarbon group; $R^{32b}$ each independently represents an unsubstituted or a substituted monovalent hydrocarbon group; $R^{42b}$ each independently represents an unsubstituted or a substituted hydrocarbon ligand, an unsubstituted or a substituted alkoxy ligands, amide ligands, and halide ligands different from —$OR^{32b}$; M' represents a metal atom or a semimetal atom; n2' represents the oxidation number of M' and (n2'-m2') is an integer of 1 to 6; m2' represents an integer of 0 or more and (n2'-1) or less; $Q^{b'}$ represents a (2/q2')-valent counter cation; and q2' is 1 or 2.

[B5] The method for producing a carbamic acid ester according to [B4], wherein $Q^{b'}$ is a cation selected from the group consisting of an ammonium cation, an amidinium cation, a guanidinium cation, a phosphonium cation, a phosphazenium cation, a carbocation, an alkali metal cation, and an alkaline earth metal cation.

[B6] The method for producing a carbamic acid ester according to any of [B1] to [B5], wherein the metal alkoxide is at least one selected from the group consisting of a titanium compound and a silicon compound.

[B7] The method for producing a carbamic acid ester according to any of [B1] to [B6], wherein the metal alkoxide is an alkoxysilane, and the reaction step is performed in the presence of a catalyst.

[B8] The method for producing a carbamic acid ester according to [B7], wherein the catalyst is at least one selected from the group consisting of an organic base carboxylic acid salt, an alkali metal salt, a zinc compound, a titanium(IV) compound, and a zirconium(IV) compound.

[B9] The method for producing a carbamic acid ester according to any of [B1] to [B8], wherein the reaction step is performed in the presence of an aprotic solvent.

[B10] The method for producing a carbamic acid ester according to any of [B1] to [B9], further comprising a carbamic acid salt production step of contacting an amino group-containing organic compound with a carbon dioxide-containing mixed gas in the presence of a base in a solvent to produce the carbamic acid salt, wherein a volume of carbon dioxide in the carbon dioxide-containing mixed gas is 0.01% or more.

In [B1] to [B9], the carbamic acid salt is preferably produced by the method for producing a carbamic acid salt according to the first aspect of the present invention.

The present inventors have made intensive studies in order to achieve the third object, and as a result, have found that a urea derivative is produced by heating a carbamic acid salt in the presence of a metal-containing catalyst or an organic base catalyst and thus have completed a third aspect of the present invention.

The third aspect of the present invention provides the following specific embodiments and the like.

[C1] A method for producing a urea derivative, comprising a reaction step of heating a carbamic acid salt in the presence of a catalyst to produce a urea derivative having a structure represented by the following formula (b'), wherein the catalyst is a metal-containing catalyst or an organic base catalyst:

(b')

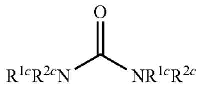

in the formula (b'), $R^{1c}$ each independently represents a hydrogen atom, or an unsubstituted or a substituted hydrocarbon group, and $R^{2c}$ each independently represents an unsubstituted or a substituted hydrocarbon group, provided that two $R^{2c}$(s) may be linked to each other to form a ring.

[C2] The method for producing a urea derivative according to [C1], wherein the carbamic acid salt is a carbamic acid salt represented by formula (A'-1), and the urea derivative having the structure represented by the formula (b') is a urea derivative represented by formula (B'-1):

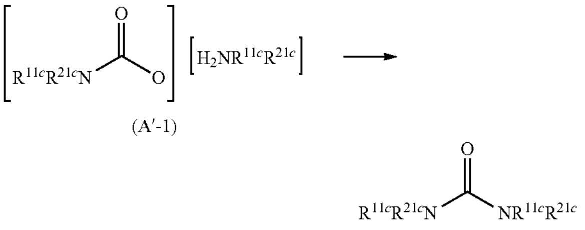

(A'-1)

(B'-1)

in the formulae (A'-1) and (B'-1), $R^{11c}$ each independently represents a hydrogen atom, or an unsubstituted or a substituted hydrocarbon group, and $R^{21c}$ each independently represents an unsubstituted or a substituted hydrocarbon group.

[C3] The method for producing a urea derivative according to [C1], wherein the carbamic acid salt is a carbamic acid salt represented by formula (A'-2), and the urea derivative having the structure represented by the formula (b') is a urea derivative represented by formula (B'-2):

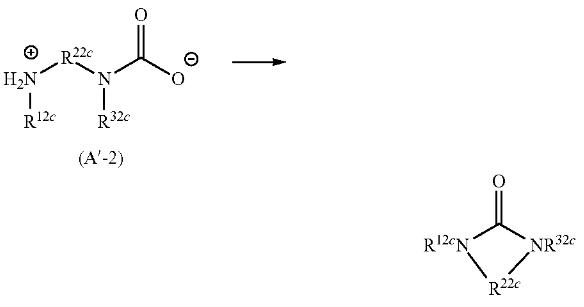

(A'-2)

(B'-2)

in the formulae (A'-2) and (B'-2), $R^{12c}$ represents a hydrogen atom, or an unsubstituted or a substituted hydrocarbon group, $R^{22c}$ represents an unsubstituted or a substituted hydrocarbon group, and $R^{32c}$ represents a hydrogen atom, or an unsubstituted or a substituted hydrocarbon group.

[C4] The method for producing a urea derivative according to any of [C1] to [C3], wherein the catalyst is at least one selected from the group consisting of a titanium-based catalyst, a tin-based catalyst, a hafnium-based catalyst, an alkali metal-based catalyst, a zinc-based catalyst, a nickel-based catalyst, and an organic base.

[C5] The method for producing a urea derivative according to any of [C1] to [C4], wherein the reaction step is performed in the presence of an aprotic polar solvent.

[C6] The method for producing a urea derivative according to any of [C1] to [C5], further comprising a carbamic acid salt production step of contacting an amino group-containing organic compound with a carbon dioxide-containing mixed gas in a solvent to produce the carbamic acid salt, wherein a volume of carbon dioxide in the carbon dioxide-containing mixed gas is 0.01% or more.

In [C1] to [C5], the carbamic acid salt is preferably produced by the method for producing a carbamic acid salt according to the first aspect of the present invention.

Advantageous Effects of the Invention

According to the first aspect of the present invention, a novel method for producing a carbamic acid salt is provided in which a carbamic acid salt can be produced from carbon dioxide at a partial pressure lower than an ordinary pressure.

According to the second aspect of the present invention, a method for producing a carbamic acid ester with a carbamic acid salt as a raw material, with neither any sacrificial reagent, nor any alkyl halide can be provided.

According to the third aspect of the present invention, a urea derivative can be produced by a catalyst reaction with a carbamic acid salt as a raw material.

MODE FOR CARRYING OUT THE INVENTION

While the detail of the present invention is described with reference to specific examples, the present invention is not limited to the following contents and can be appropriately modified and carried out without departing from the gist thereof.

Hereinafter, the first aspect of the present invention will be described.

<A: 1. Method for Producing Carbamic Acid Salt>

A method for producing a carbamic acid salt according to one embodiment of the first aspect of the present invention includes contacting a carbon dioxide-containing mixed gas having a partial pressure of carbon dioxide of 0.001 atm or more and less than 1 atm with an amino group-containing organic compound in the presence of a base in at least one organic solvent selected from the group consisting of an organic solvent having 2 or more and 8 or less carbon atoms.

According to the present embodiment, a carbamic acid salt can be produced from carbon dioxide at a partial pressure lower than an ordinary pressure. A carbamic acid salt can be produced from a carbon dioxide mixed gas having a low concentration of about 15%, at a high yield for a relatively short time. A carbamic acid salt obtained by the production method according to the present embodiment can be used for synthesizing a urea derivative and a carbamic acid ester. Accordingly, the production method according to the present embodiment can serve as a technique for converting a low-concentration carbon dioxide included in an exhaust gas or the like, into a useful chemical product.

Hereinafter, the "carbamic acid salt", "amino group-containing organic compound", "base", "solvent", "carbon dioxide-containing mixed gas", and the like will be described. A step of contacting a carbon dioxide-containing mixed gas and an amino group-containing organic compound in the presence of a base in a solvent to produce a carbamic acid salt is simply referred to as "reaction step" herein in the description of the first aspect of the present invention.

<A: 1-1. Carbamic Acid Salt>

A carbamic acid salt produced by the production method according to the present embodiment is not particularly limited, and may be determined depending on objects.

The method for producing a carbamic acid salt according to the present embodiment can suitably produce, for example, a compound represented by the following general formula (a) or a compound represented by the following general formula (b).

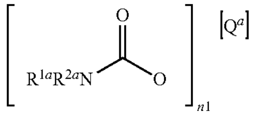

(a)

In the formula (a), $R^{1a}$ represents a hydrogen atom, an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom; $R^{2a}$ represents an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom; $Q^a$ represents an n1-valent counter cation derived from a base, and is an ammonium cation, an amidinium cation, a guanidinium cation, a phosphonium cation, a phosphazenium cation, a carbocation, an alkali metal cation, or an alkaline earth metal cation; and n1 is 1 or 2.

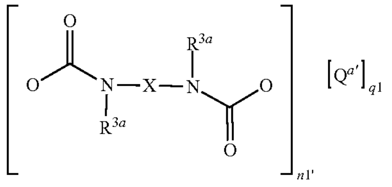

(b)

In the formula (b), $R^{3a}$ each independently represents a hydrogen atom, an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom; X represents a divalent hydrocarbon group which may contain an oxygen atom and/or a nitrogen atom; $Q^{a'}$ represents an n1'-valent counter cation derived from a base, and is an ammonium cation, an amidinium cation, a guanidinium cation, a phosphonium cation, a phosphazenium cation, a carbocation, an alkali metal cation, or an alkaline earth metal cation; n1' is 1 or 2; and q1 is 2 when n1' is 1, and q1 is 1 when n1' is 2. Hereinafter, the compound represented by the formula (a) or (b) will be described.

<A: 1-1-1. Compound Represented by Formula (a)>

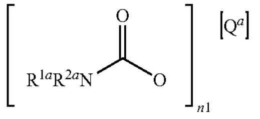

(a)

In the formula (a), $R^{1a}$ represents a hydrogen atom, an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom.

The “hydrocarbon group” in the description of the first aspect of the present invention is not herein limited to a linear saturated hydrocarbon group, and may have each of a carbon-carbon unsaturated bond, a branched structure, and a cyclic structure.

The number of carbon atoms in $R^{1a}$ of the hydrocarbon group is not particularly limited, and is usually 1 or more, and usually 50 or less, preferably 40 or less, more preferably 30 or less.

Examples of the such hydrocarbon group represented by $R^{1a}$ include an alkyl group such as a methyl group, an ethyl group, a n-propyl group, an iso-propyl group, a n-butyl group, a sec-butyl group, an iso-butyl group, a tert-butyl group, a n-pentyl group, an iso-pentyl group, a neopentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-docosyl group; a cycloalkyl group such as a cyclopropyl group, a cyclobutyl group, a cyclopentyl group and a cyclohexyl group; and an aromatic hydrocarbon group such as a phenyl group, a 1-naphthyl group, a 2-naphthyl group, a 1-phenanthryl group, a 2-phenanthryl group, a 3-phenanthryl group, a 4-phenanthryl group, a 9-phenanthryl group, a 1-anthryl group, a 2-anthryl group, a 9-anthryl group, a 1-pyrenyl group, a 2-pyrenyl group, a 4-pyrenyl group, a 1-triphenylenyl group and a 2-triphenylenyl group.

The hydrocarbon group as the substituent is not particularly limited, and examples thereof include an alkyl group each having 1 to 4 carbon atoms, such as a methyl group, an ethyl group, a n-propyl group, an isopropyl group, a n-butyl group, a sec-butyl group, an isobutyl group and a tert-butyl group; a cycloalkyl group each having 3 to 4 carbon atoms, such as a cyclopropyl group and a cyclobutyl group; and an aromatic hydrocarbon group each having 6 to 10 carbon atoms, such as a phenyl group, a 1-naphthyl group and a 2-naphthyl group.

The oxygen-containing functional group may be any functional group containing an oxygen atom, and examples thereof include an alkoxy group, a carboxy group, a carbonyl group, a ketone group, an ether group, and a hydroxyl group.

The nitrogen-containing functional group may be any functional group containing a nitrogen atom, and is preferably a nitrogen-containing functional group other than an amino group. Examples include an ammonium group, an amidino group, a pyrrolyl group, a triazine ring, a triazole ring, a benzotriazolyl group, an imidazolyl group, a benzimidazolyl group, a quinolyl group, a pyridyl group, a pyrimidine group, a pyrazinyl group, a quinazolinyl group, a quinoxalinyl group, a purinyl group, a piperidinyl group, a piperazinyl group, a pyrrolidinyl group, a pyrazolyl group, an aniline group, an azo group, a diazo group, an azide group, and a cyano group.

Examples of the functional group containing an oxygen atom and a nitrogen atom include an amide group, an imide group, a urea group, a group including an isocyanuric structure, a nitro group, a nitroso group, a cyanate group, an isocyanate group, a morpholino group, and a lactam ring.

When the hydrocarbon group has a substituent, the number of carbon atoms means the total number of carbon atoms of the number of carbon atoms in the substituent and the number of carbon atoms in the hydrocarbon group.

When the hydrocarbon group represented by $R^{1a}$ has a substituent, examples of $R^{1a}$ can preferably include an aralkyl group such as a benzyl group, a phenethyl group, a 1-naphthylmethyl group and a 2-naphthylmethyl group; a cycloalkylalkyl group such as a cyclohexylmethyl group; a hydrocarbon group each having an oxygen-containing functional group, such as a furfuryl group; and a hydrocarbon group each having a nitrogen-containing functional group, such as a pyridylmethyl group.

$R^{1a}$ is preferably a hydrogen atom from the viewpoint of usefulness of a carbamic acid salt.

($R^{2a}$)

In the formula (a), $R^{2a}$ represents an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom.

The number of carbon atoms of $R^{2a}$ is not particularly limited, and is usually 1 or more, and usually 50 or less, preferably 40 or less, more preferably 30 or less.

Examples of the unsubstituted hydrocarbon group represented by $R^{2a}$ include groups exemplified with respect to $R^{1a}$.

When the hydrocarbon group represented by $R^{2a}$ has a substituent, examples of the substituent include groups exemplified with respect to $R^{1a}$. When the hydrocarbon group has a substituent, the number of carbon atoms means the total number of carbon atoms of the number of carbon atoms in the substituent and the number of carbon atoms in the hydrocarbon group. When the hydrocarbon group represented by $R^{2a}$ has a substituent, examples of $R^{2a}$ can preferably include an aralkyl group such as a benzyl group, a phenethyl group, a 1-naphthylmethyl group and a 2-naphthylmethyl group; a cycloalkylalkyl group such as a cyclohexylmethyl group; a hydrocarbon group having an oxygen-containing functional group, such as a furfuryl group; and a hydrocarbon group having a nitrogen-containing functional group, such as a pyridylmethyl group.

$R^{2a}$ is preferably an alkyl group such as a n-hexyl group; a cycloalkyl group such as a cyclohexyl group, an aromatic hydrocarbon group such as a phenyl group, or an aralkyl group such as a benzyl group, more preferably a n-hexyl group, a cyclohexyl group, a phenyl group, or a benzyl group, from the viewpoint of availability of raw materials.

($Q^{a}$)

In the formula (a), $Q^{a}$ represents a base-derived n1-valent counter cation, and represents an ammonium cation, an amidinium cation, a guanidinium cation, a phosphonium cation, a phosphazenium cation, a carbocation, an alkali metal cation, or an alkaline earth metal cation. Accordingly, n1 is 1 or 2.

Examples of the ammonium cation include a primary ammonium cation such as a n-butylammonium cation; a secondary ammonium cation such as a diethylammonium cation; a tertiary ammonium cation such as a triethylammonium cation; and a quaternary ammonium cation such as a tetramethylammonium cation, a phenyltrimethylammonium cation and a tetrabutylammonium cation.

Examples of the amidinium cation include a formamidinium cation, an acetamidinium cation, a 1,5-diazabicyclo[4.3.0]non-5-enium cation, and a 1,8-diazabicyclo[5.4.0]undec-7-enium cation respectively obtained by protonation of formamidine, acetamidine, 1,5-diazabicyclo[4.3.0]non-5-ene, and 1,8-diazabicyclo[5.4.0]undec-7-ene, as well as derivatives thereof each having one or more substituents. Examples of such a substituent include hydrocarbon groups such as alkyl groups, cycloalkyl groups, and aromatic hydrocarbon groups, exemplified in the description of the section ($R^{1a}$).

Examples of the guanidinium cation include a 1,1,3,3-tetramethyl guanidinium cation, a 2-tert-butyl-1,1,3,3-tetramethyl guanidinium cation, a 1,5,7-triazabicyclo[4.4.0]dec-5-enium cation, and a 7-methyl-1,5,7-triazabicyclo[4.4.0]dec-5-enium cation respectively obtained by protonation of 1,1,3,3-tetramethylguanidine, 2-tert-butyl-1,1,3,3-tetramethylguanidine, 1,5,7-triazabicyclo[4.4.0]dec-5-ene, and 7-methyl-1,5,7-triazabicyclo[4.4.0]dec-5-ene, as well as derivatives thereof each having one or more substituents. Examples of such a substituent include hydrocarbon groups such as alkyl groups, cycloalkyl groups, and aromatic hydrocarbon groups, exemplified in the description of the section ($R^{1a}$).

Examples of the phosphonium cation include a tertiary phosphonium cation such as a triphenyl phosphonium cation and a tri-tert-butyl phosphonium cation; and a quaternary phosphonium cation such as a tetraphenyl phosphonium cation, a tetra-p-tolyl phosphonium cation, a triphenylbenzyl phosphonium cation, a triphenylbutyl cation, a tetraethylphosphonium cation and a tetrabutylphosphonium cation.

Examples of the phosphazenium cation include a tert-butylimino-tris(dimethylamino)phosphoranium cation, a tert-butylimino-tri(pyrrolidino)phosphoranium cation, a 2-tert-butylimino-2-diethylamino-1,3-dimethylperhydro-1,3,2-diazaphosphorinium cation, a 1-tert-butyl-2,2,4,4,4-pentakis(dimethylamino)-2λ$^5$,4λ$^5$-catenadi(phosphazenium), and a 1-tert-butyl-4,4,4-tris(dimethylamino)-2,2-bis[tris(dimethylamino)phosphoranylideneamino]-2λ$^5$,4λ$^5$-catenadi(phosphazenium) cation respectively obtained by protonation of tert-butylimino-tris(dimethylamino)phosphorane, tert-butylimino-tri(pyrrolidino)phosphorane, 2-tert-butylimino-2-diethylamino-1,3-dimethylperhydro-1,3,2-diazaphosphorine, 1-tert-butyl-2,2,4,4,4-pentakis(dimethylamino)-2λ$^5$,4λ$^5$-catenadi(phosphazene), and 1-tert-butyl-4,4,4-tris(dimethylamino)-2,2-bis[tris(dimethylamino)phosphoranylideneamino]-2λ$^5$,4λ$^5$-catenadi(phosphazene), as well as derivatives thereof each having one or more substituents. Examples of such a substituent include hydrocarbon groups such as alkyl groups, cycloalkyl groups, and aromatic hydrocarbon groups, exemplified in the description of the section ($R^{1a}$).

Examples of the carbocation include monovalent carbocations such as a triphenylmethyl cation, a tropylium cation, and an azulenium cation.

Examples of the alkali metal cation include a lithium cation, a sodium cation, and a potassium cation.

Examples of the alkaline earth metal cation include a magnesium cation and a calcium cation.

An ammonium cation, an amidinium cation, a guanidinium cation, a phosphonium cation, a phosphazenium cation, or a carbocation is preferable, and an ammonium cation, an amidinium cation, a guanidinium cation, a phosphonium cation, or a phosphazenium cation is more preferable, from the viewpoint of availability of raw materials. In particular, an ammonium cation or an amidinium cation is preferable.

The amino group-containing organic compound in the present embodiment may be a base or may be an ammonium cation produced by reception of a proton by the amino group-containing organic compound. The amino group-containing organic compound in the present embodiment may also serve as a base or may be a carbamic acid salt having a carbamic acid ion moiety and an ammonium cation moiety in one molecule.

(n1)

In the formula (a), n1 is 1 or 2. n1 represents the number of carbamic anions, and is a value equal to the valence of $Q^a$. Accordingly, when $Q^a$ is a monovalent cation, n1 is 1, and when $Q^a$ is a divalent cation, n1 is 2.

Specific examples of the compound represented by the formula (a) include methylammonium N-methylcarbamate, ethylammonium N-ethylcarbamate, propylammonium N-propylcarbamate, butylammonium N-butylcarbamate, pentylammonium N-pentylcarbamate, hexylammonium N-hexylcarbamate, benzylammonium N-benzylcarbamate, phenylammonium N-phenylcarbamate, and a compound represented by the following formula, and an amidinium salt, a guanidinium salt, a phosphonium salt, a phosphazenium salt, a carbocation salt, an alkali metal salt, or an alkaline earth metal salt thereof in which each counter cation is, respectively, an amidinium cation other than a 1,8-diazabicyclo[5.4.0]undec-7-enium cation, a guanidinium cation, a phosphonium cation, a phosphazenium cation, a carbocation, an alkali metal cation, or an alkaline earth metal cation, but are not limited thereto.

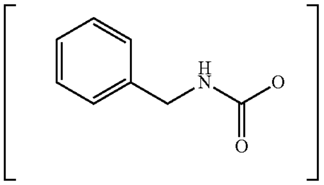

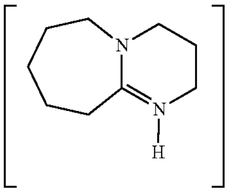

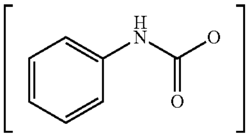

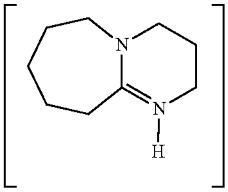

<A: 1-1-2. Compound Represented by Formula (b)>

(b)

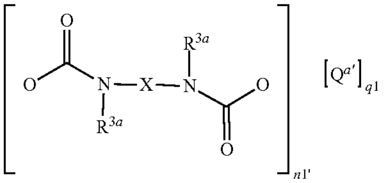

($R^{3a}$)

In the formula (b), $R^{3a}$ each independently represents a hydrogen atom, an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom.

Examples of the unsubstituted hydrocarbon group represented by $R^{3a}$ include groups exemplified with respect to $R^{1a}$ in <A: 1-1-1. Compound represented by formula (a)>.

When the hydrocarbon group represented by $R^{3a}$ has a substituent, examples of the substituent include groups exemplified with respect to $R^{1a}$ in <A: 1-1-1. Compound represented by formula (a)>. When the hydrocarbon group has a substituent, the number of carbon atoms means the total number of carbon atoms of the number of carbon atoms in the substituent and the number of carbon atoms in the hydrocarbon group. When the hydrocarbon group represented by $R^{3a}$ has a substituent, examples of $R^{3a}$ can preferably include a benzyl group.

Two $R^{3a}$(s) may be the same as each other or different from each other, and are preferably the same as each other from the viewpoints of ease of synthesis and of economy. It is preferred that at least one $R^{3a}$ is a hydrogen atom or a methyl group, and it is more preferred that each of both two $R^{3a}$(s) is a hydrogen atom or a methyl group, from the viewpoint of usefulness of a carbamic acid salt.

(X)

In the formula (b), X represents a divalent hydrocarbon group which may contain an oxygen atom and/or a nitrogen atom. The X "which may contain an oxygen atom or a nitrogen atom" not only means that a functional group containing an oxygen atom and/or a nitrogen atom, such as a nitro group ($—NO_2$), an epoxy group, a hydroxyl group (—OH), a carbonyl group (—C(═O)—), or an azide group ($—N_3$), may be contained as a substituent, but also means that a linking group containing an oxygen atom or a nitrogen atom, such as an ether group (—O—), may be contained inside a carbon backbone. In other words, a carbon atom forming a backbone of a divalent hydrocarbon group may be substituted with an oxygen atom or a nitrogen atom. Accordingly, for example, a hydrocarbon group having 2 carbon atoms, as X, encompasses a hydrocarbon group having 2 carbon atoms, containing a hydroxyl group such as $—CH_2—CH(OH)—$, and a hydrocarbon group having 2 carbon atoms, containing an ether group inside a carbon backbone such as $—CH_2—O—CH_2—$. When X has a substituent, the number of carbon atoms in X includes the number of carbon atoms contained in the substituent.

Examples of the divalent hydrocarbon group include a hydrocarbon group including at least one of an aliphatic hydrocarbon group and an aromatic hydrocarbon group; preferably a group including at least one selected from an aliphatic hydrocarbon group having 1 to 20 carbon atoms and an aromatic hydrocarbon group having 6 to 20 carbon atoms; more preferably a group selected from an aliphatic hydrocarbon group having 1 to 20 carbon atoms, an aromatic hydrocarbon group having 6 to 20 carbon atoms, and a group which includes an aliphatic hydrocarbon group having 1 to 20 carbon atoms and an aromatic hydrocarbon group having 6 to 20 carbon atoms; further preferably a group selected from an aliphatic hydrocarbon group having 1 to 20 carbon atoms, an aromatic hydrocarbon group having 6 to 20 carbon atoms, and a group which has 7 to 20 carbon atoms consisting of an aliphatic hydrocarbon group and an aromatic hydrocarbon group. Specific examples of the divalent aliphatic hydrocarbon group include a linear hydrocarbon group such as a methylene group, an ethylene group, a tetramethylethylene group, a n-propylene group (trimethylene group), a 1-methylpropylene group, a 1,1-dimethylpropylene group, a 2-methylpropylene group, a 1,2-dimethylpropylene group, a 2,2-dimethylpropylene group, a 1,1,2-trimethylpropylene group, a 1,1,3-trimethylpropylene group, a n-butylene group (tetramethylene group), a 2-methyl-1,4-butylene group, a 3-methyl-1,4-butylene group, a 2,2-dimethyl-1,4-butylene group, a 2,3-dimethyl-1,4-butylene group, a 2,2,3-trimethyl-1,4-butylene group, a n-pentylene group (pentamethylene group) and a n-hexanylene group (hexamethylene group); and an alicyclic hydrocarbon group such as a 1,4-cyclohexylene group. Specific examples of the divalent aromatic hydrocarbon group include a 1,4-phenylene group, a 1,2-phenylene group and a 1,3-phenylene group, each of which is obtained by removal of two hydrogen atoms from a benzene ring; and a dimethylphenylene group (xylyl group) obtained by removal of two hydrogen atoms from a benzene ring of xylene, a methylphenylene group (tolylene group) obtained by removal of two hydrogen atoms from a benzene ring of toluene, and a naphthanylene group obtained by removal of two hydrogen atoms from naphthalene. Specific examples of the group including an aliphatic hydrocarbon group and an aromatic hydrocarbon group include a 1,4-phenylenebis(methylene) group, a 1,4-phenylenebis(ethylene) group, a group obtained by removal of one hydrogen atom from each of two benzene rings of biphenyl, and a group obtained by removal of one hydrogen atom from each of two benzene rings of diphenylmethane.

X is particularly preferably an aliphatic hydrocarbon group having 1 to 20 carbon atoms, or a group which has 7 to 20 carbon atoms includes an aliphatic hydrocarbon group and an aromatic hydrocarbon group; most preferably an aliphatic hydrocarbon group having 2 to 20 carbon atoms, and in particular, preferably a hexamethylene group having 6 carbon atoms, from the viewpoint of usefulness of a carbamic acid salt.

($Q^{a'}$)

In the formula (b), $Q^{a'}$ represents a base-derived n1'-valent counter cation, and represents an ammonium cation, an amidinium cation, a guanidinium cation, a phosphonium cation, a phosphazenium cation, a carbocation, an alkali metal cation, or an alkaline earth metal cation. Accordingly, n1' is 1 or 2. Specific examples of $Q^{a'}$ include cations exemplified in <A: 1-1-1. Compound represented by formula (a)>. An ammonium cation, an amidinium cation, a guanidinium cation, a phosphonium cation, a phosphazenium cation, a carbocation, an alkali metal cation, or an alkaline earth metal cation is preferable, and an ammonium cation, an amidinium cation, a guanidinium cation, or a phosphazenium cation is more preferable, from the viewpoint of ease of synthesis. In particular, a tert-butylimino-tri(pyrrolidino)phosphoranium cation or a 1,8-diazabicyclo[5.4.0]undec-7-enium cation is preferable.

(n1')

In the formula (b), n1' is 1 or 2. n1' represents the number of carbamic anions, and is a value equal to the valence of $Q^{a'}$. Accordingly, when $Q^{a'}$ is a monovalent cation, n1' is 1, and when $Q^{a'}$ is a divalent cation, n1' is 2.

(q1)

In the formula (b), q1 represents the number of cation $Q^{a'}$(s), and when $Q^{a'}$ represents a monovalent cation, namely, when n1' is 1, q1 is 2, and when $Q^{a'}$ represents a divalent cation, namely, when n1' is 2, q1 is 1.

Specific examples of the compound represented by the formula (b) include a compound represented by the following formula, and an amidinium salt, a guanidinium salt, a phosphonium salt, a phosphazenium salt, a carbocation salt, an alkali metal salt, or an alkaline earth metal salt thereof in which each counter cation is, respectively, an amidinium cation other than a 1,8-diazabicyclo[5.4.0]undec-7-enium cation, a guanidinium cation, a phosphonium cation, a phosphazenium cation, a carbocation, an alkali metal cation, or an alkaline earth metal cation, but are not limited thereto.

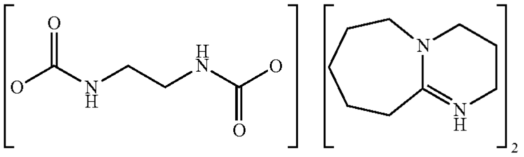

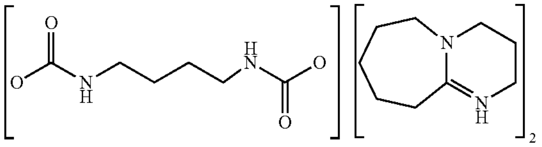

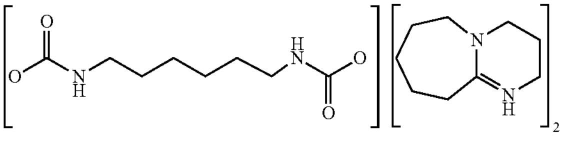

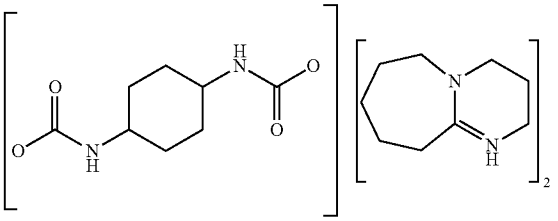

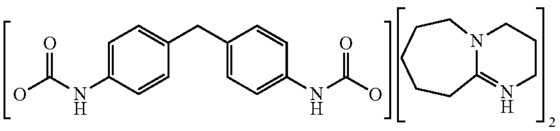

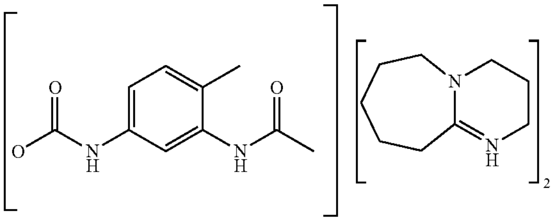

Specific examples of the compound represented by the formula (b) also include a compound represented by the following formula, and an amidinium salt, a guanidinium salt, a phosphonium salt, a phosphazenium salt, a carbocation salt, an alkali metal salt, or an alkaline earth metal salt thereof in which each counter cation is, respectively, an amidinium cation, a guanidinium cation, a phosphonium cation, a phosphazenium cation other than tert-butylimino-tri(pyrrolidino)phosphoranium cation, a carbocation, an alkali metal cation, or an alkaline earth metal cation, but are not limited thereto.

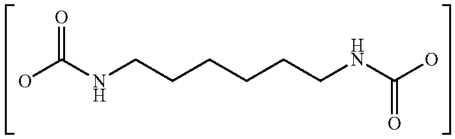

-continued

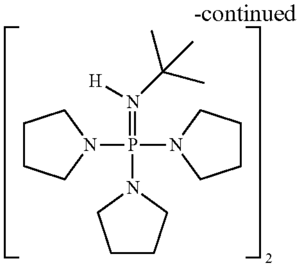

<A: 1-2. Amino Group-Containing Organic Compound>

The amino group-containing organic compound for use in the present embodiment is not particularly limited, and one which produces an objective carbamic acid salt may be appropriately selected.

Examples of the amino group-containing organic compound preferably include an amino group-containing organic compound represented by formula (B) or (C).

<A: 1-2-1. Amino Group-Containing Organic Compound Represented by Formula (B)>

$$R^{11a}R^{21a}NH \quad (B)$$

In the formula (B), $R^{11a}$ represents a hydrogen atom, an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom; and $R^{21a}$ represents an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom.

($R^{11a}$)

$R^{11a}$ represents a hydrogen atom, an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom.

Examples of the unsubstituted hydrocarbon group represented by $R^{11a}$ include groups exemplified with respect to $R^{1a}$.

When the hydrocarbon group represented by $R^{11a}$ has a substituent, examples of the substituent include groups exemplified with respect to $R^{1a}$. When the hydrocarbon group has a substituent, the number of carbon atoms means the total number of carbon atoms of the number of carbon atoms in the substituent and the number of carbon atoms in the hydrocarbon group. When the hydrocarbon group represented by $R^{11a}$ has a substituent, examples of $R^{11a}$ can preferably include a benzyl group.

$R^{11a}$ is preferably a hydrogen atom from the viewpoint of usefulness of a carbamic acid salt.

($R^{21a}$)

$R^{21a}$ represents an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom.

Examples of the unsubstituted hydrocarbon group represented by $R^{21a}$ include groups exemplified with respect to $R^{1a}$.

When the hydrocarbon group represented by $R^{21a}$ has a substituent, examples of the substituent include groups exemplified with respect to $R^{1a}$. When the hydrocarbon group has a substituent, the number of carbon atoms means the total number of carbon atoms of the number of carbon atoms in the substituent and the number of carbon atoms in the hydrocarbon group. When the hydrocarbon group represented by $R^{21a}$ has a substituent, examples of $R^{21a}$ include groups exemplified with respect to $R^{2a}$, and a benzyl group is more preferable.

$R^{21a}$ is preferably an alkyl group such as a n-hexyl group; a cycloalkyl group such as a cyclohexyl group; an aromatic hydrocarbon group such as a phenyl group; and an aralkyl group such as a benzyl group; more preferably a n-hexyl group, a cyclohexyl group, a phenyl group, and a benzyl group, from the viewpoint of availability of raw materials.

Examples of the amino group-containing organic compound represented by the formula (B) include monoamine compounds such as benzylamine, hexylamine, dimethylamine, diethylamine, ethylmethylamine, cyclohexylamine and aniline.

<A: 1-2-2. Amino Group-Containing Organic Compound Represented by Formula (C)>

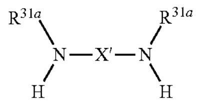

(C)

In the formula (C), $R^{31a}$ each independently represents a hydrogen atom, an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom; and X' represents a divalent hydrocarbon group which may contain an oxygen atom and/or a nitrogen atom.

($R^{31a}$)

$R^{31a}$ each independently represents a hydrogen atom, an unsubstituted hydrocarbon group, or a substituted hydrocarbon group having at least one selected from a hydrocarbon group, an oxygen-containing functional group, a nitrogen-containing functional group, and a functional group containing an oxygen atom and a nitrogen atom.

Examples of the unsubstituted hydrocarbon group represented by $R^{31a}$ include groups exemplified with respect to $R^{1a}$.

When the hydrocarbon group represented by $R^{31a}$ has a substituent, examples of the substituent include groups exemplified with respect to $R^{1a}$. When the hydrocarbon group has a substituent, the number of carbon atoms means the total number of carbon atoms of the number of carbon atoms in the substituent and the number of carbon atoms in the hydrocarbon group. When the hydrocarbon group represented by $R^{31a}$ has a substituent, examples of $R^{31a}$ can preferably include a benzyl group.

Two $R^{31a}$(s) may be the same as each other or different from each other, and are preferably the same as each other from the viewpoints of ease of synthesis and of economy. It is preferred that at least one $R^{31a}$ is a hydrogen atom or a methyl group, and it is more preferred that each of both two $R^{31a}$(s) is a hydrogen atom or a methyl group, from the viewpoint of usefulness of a carbamic acid salt.

(X')

X' represents a divalent hydrocarbon group which may contain an oxygen atom and/or a nitrogen atom. The X' "which may contain an oxygen atom or a nitrogen atom" is applied by the description in the section <A: 1-1-2. Compound represented by formula (b)>.

X' is preferably a group containing at least one selected from an aliphatic hydrocarbon group having 1 to 20 carbon atoms and an aromatic hydrocarbon group having 6 to 20 carbon atoms; more preferably a group selected from an aliphatic hydrocarbon group having 1 to 20 carbon atoms, an aromatic hydrocarbon group having 6 to 20 carbon atoms, and a group which includes an aliphatic hydrocarbon group having 1 to 20 carbon atoms and an aromatic hydrocarbon group having 6 to 20 carbon atoms; further preferably a group selected from an aliphatic hydrocarbon group having 1 to 20 carbon atoms, an aromatic hydrocarbon group having 6 to 20 carbon atoms, and a group which has 7 to 20 carbon atoms consisting of an aliphatic hydrocarbon group and an aromatic hydrocarbon group; particularly preferably an aliphatic hydrocarbon group having 1 to 20 carbon atoms, or a group which has 7 to 20 carbon atoms consisting of an aliphatic hydrocarbon group and an aromatic hydrocarbon group; most preferably an aliphatic hydrocarbon group having 2 to 20 carbon atoms, and in particular, preferably a hexamethylene group having 6 carbon atoms. Specific examples of the aliphatic hydrocarbon group and the aromatic hydrocarbon group include groups described above in <A: 1-1-2. Compound represented by formula (b)>.

Specific examples of the amino group-containing organic compound represented by the formula (C) include methylenediamine, ethylenediamine, propylenediamine, hexylenediamine (hexamethylenediamine), phenylenediamine, and 4,4'-diaminodiphenylmethane, but are not limited thereto.

When the amino group-containing organic compound represented by the formula (C) is used, a mode is also preferable where a basic compound other than the amino group-containing organic compound is used as a base from the viewpoints of ease of synthesis and of economy.

<A: 1-2-3. Amount of Use of Amino Group-Containing Organic Compound>

The amount of use (amount of charging) of the amino group-containing organic compound is not particularly limited, and the concentration in a solvent is preferably 0.01 mol/L or more and 10.00 mol/L or less from the viewpoint of the yield of a carbamic acid salt When the amino group-containing organic compound in the present embodiment is a monoamine compound, the monoamine compound is also used as a base. In this case, the concentration of the monoamine compound in a solvent is preferably 0.01 mol/L or more, more preferably 0.1 mol/L or more, and preferably 1.00 mol/L or less, more preferably 0.6 mol/L or less.

When the amino group-containing organic compound in the present embodiment is a monoamine compound, an organic strong base other than the monoamine compound is used as a base. In this case, the concentration of the monoamine compound in a solvent is preferably 0.01 mol/L or more, more preferably 0.1 mol/L or more, and preferably 1.00 mol/L or less, more preferably 0.7 mol/L or less, further preferably 0.6 mol/L or less.

When the amino group-containing organic compound in the present embodiment is a diamine compound, the diamine compound is also used as a base. In this case, the concentration of the diamine compound in a solvent is preferably 1.1 mol/L or more, and 10.0 mol/L or less, more preferably 4.0 mol/L or less.

When the amino group-containing organic compound in the present embodiment is a diamine compound, an organic strong base other than the diamine compound is used as a base. In this case, the concentration of the diamine compoundpound in a solvent is preferably 0.01 mol/L or more, more preferably 0.1 mol/L or more, and preferably 10.0 mol/L or less, more preferably 4.0 mol/L or less.

<A: 1-3. Base>

The reaction step is performed in the presence of a base.

The amino group-containing organic compound is usually a basic compound, and thus the amino group-containing organic compound in the present embodiment may also be used as the base. A basic compound other than the amino group-containing organic compound in the present embodiment may also be used as the base.

The reaction step in the present embodiment is preferably performed in the presence of at least one base selected from the group consisting of an organic base, an alkali metal salt, and an alkaline earth metal salt.

Examples of the organic base include the amino group-containing organic compound, and a basic compound other than the amino group-containing organic compound. Examples of the basic compound other than the amino group-containing organic compound include organic strong bases such as 1,1,3,3-tetramethylguanidine, 2-tert-butyl-1,1,3,3-tetramethylguanidine, 1,8-diazabicyclo[5.4.0]undec-7-ene, 1,5-diazabicyclo[4.3.0]non-5-ene, 7-methyl-1,5,7-triazabicyclo[4.4.0]dec-5-ene, 1,5,7-triazabicyclo[4.4.0]dec-5-ene, tert-butylimino-tris(dimethylamino)phosphorane, tert-butylimino-tri(pyrrolidino)phosphorane, 2-tert-butylimino-2-diethylamino-1,3-dimethylperhydro-1,3,2-diazaphosphorine, 1-tert-butyl-2,2,4,4,4-pentakis(dimethylamino)-$2\lambda^5$,$4\lambda^5$-catenadi(phosphazene), and 1-tert-butyl-4,4,4-tris(dimethylamino)-2,2-bis[tris(dimethylamino) phosphoranylideneamino]-$2\lambda^5$,$4\lambda^5$-catenadi(phosphazene); pyridine; and triethylamine. In particular, organic strong bases are preferable, and 1,8-diazabicyclo[5.4.0]undec-7-ene is more preferable.

Examples of the alkali metal salt include alkali metal acetates such as lithium acetate, sodium acetate, potassium acetate, rubidium acetate and cesium acetate; alkali metal carbonates such as lithium carbonate, sodium carbonate, potassium carbonate, rubidium carbonate and cesium carbonate; alkali metal hydroxides such as lithium hydroxide, sodium hydroxide, potassium hydroxide, rubidium hydroxide and cesium hydroxide; and alkali metal alkoxides such as lithium alkoxide, sodium alkoxide, potassium alkoxide, rubidium alkoxide and cesium alkoxide.

Examples of the alkaline earth metal salt include alkaline earth metal acetates such as calcium acetate, strontium acetate and barium acetate; alkaline earth metal carbonates such as calcium carbonate, strontium carbonate and barium carbonate; alkaline earth metal hydroxides such as calcium hydroxide, strontium hydroxide and barium hydroxide; and alkaline earth metal alkoxides such as calcium alkoxide, strontium alkoxide and barium alkoxide.

When the basic compound other than the amino group-containing organic compound is used as the base, the amount of use (amount of charging) of the base is usually 1 equivalent or more, and usually 15 equivalents or less, preferably 10 equivalents or less, more preferably 5 equivalents or less, further preferably 3 equivalent or less, relative to 1 equivalent of an amino group of the amino group-containing organic compound.

<A: 1-4. Solvent>

The reaction step is performed in a solvent. The solvent is at least one selected from the group consisting of an organic solvent having 2 or more and 8 or less carbon atoms, and two or more thereof may be used in combination.

Examples of the organic solvent having 2 or more and 8 or less carbon atoms include alcohols such as ethanol, propanol, isopropanol, 1-butanol, 2-butanol, isobutanol, t-butanol, allyl alcohol, ethylene glycol, 1,2-propanediol, 1,3-propanediol, 1,2-butanediol, 1,3-butanediol, 1,4-butanediol and glycerin; ethers such as diethyl ether, tetrahydrofuran and 1,4-dioxane; hydrocarbon-based solvents such as n-hexane, cyclohexane, n-octane, benzene, toluene and xylene; nitriles such as acetonitrile, propionitrile, butyronitrile and isobutyronitrile; and aprotic polar solvents such as dimethylacetamide, N,N-dimethylformamide, N,N'-dimethylpropylene urea, 1,3-dimethyl-2-imidazolidinone and N-methylpyrrolidone. Alcohols, ethers, hydrocarbon-based solvents, or aprotic polar solvents are preferable, and ethanol, hexane, 1,4-dioxane, or N-methylpyrrolidone is more preferable. The reaction solvent can be used to thereby more efficiently produce a carbamic acid salt. The amount of use of the solvent is not particularly limited, may be appropriately adjusted depending on the reaction scale, and is preferably in the range described in <A: 1-2. Amino group-containing organic compound>.

<A: 1-5. Carbon Dioxide-Containing Mixed Gas>

A carbon dioxide-containing mixed gas for use in the reaction step is a carbon dioxide-containing mixed gas having a partial pressure of carbon dioxide of 0.001 atm or more and less than 1 atm. The partial pressure of carbon dioxide in the carbon dioxide-containing mixed gas is preferably 0.01 atm or more, more preferably 0.05 atm or more, further preferably 0.10 atm or more, particularly preferably 0.15 atm or more, most preferably 0.20 atm or more, and is preferably 0.50 atm or less, from the viewpoint of the reaction efficiency. Examples of any gas other than carbon dioxide, which can be included in the carbon dioxide-containing mixed gas, include inert gases such as nitrogen and argon; and oxygen. The pressure (total pressure) in the reaction step is usually 0.01 atm or more, preferably 0.05 atm or more, more preferably 0.5 atm or more, and usually 10 atm or less, preferably 5 atm or less, more preferably 2 atm or less, further preferably 1.2 atm or less, and is particularly preferably 1±0.1 atm. An exhaust gas or the like can be used as the carbon dioxide-containing mixed gas, and production of a carbamic acid salt by the production method according to the present embodiment is effective for the reduction of greenhouse gas emissions and enables effective utilization of low-concentration carbon dioxide.

<A: 1-6. Other Reaction Conditions and the Like>

The reaction step is made by, for example, placing the amino group-containing organic compound and the solvent into a sealed reaction vessel, blowing a carbon dioxide-containing gas thereinto to produce a carbamic acid salt. In the present embodiment, for example, when the volume of carbon dioxide in the carbon dioxide-containing mixed gas in the solvent is 15%, 1 mmol of the amino group-containing organic compound as a raw material can be reacted for 5 minutes or more and 10 minutes or less to synthesize a carbamic acid salt at a yield of 80% or more. When 40 mmol of the amino group-containing organic compound is used, a yield of 90% or more can be achieved by a reaction time of about 180 minutes. Such a carbamic acid salt produced can be easily isolated by filtration. The temperature in the reaction step is not particularly limited, and is usually 5° C. to 45° C., preferably around a room temperature of 15° C. to 25° C. from the viewpoint of economy.

(Reaction Time)

The reaction time is not particularly limited, and may be appropriately adjusted depending on the reaction temperature, the reaction scale, and the like. The reaction time is usually 5 minutes or more, preferably 10 minutes or more, and usually 48 hours or less, preferably 24 hours or less, more preferably 20 hours or less, further preferably 3 hours or less. In particular, when the diamine compound is used as the amino group-containing organic compound and any of alcohols is used as the solvent, a carbamic acid salt can be synthesized at a high yield by use of a low-concentration carbon dioxide gas containing about 15% by volume of carbon dioxide even under a condition of room temperature for a reaction time of 30 minutes or less.

(Reaction Vessel)

The reaction vessel is not particularly limited, and is required to be appropriately selected depending on a continuous process or a batch process. A continuous process or a batch process may be adopted in the present embodiment. In the case of a batch process, a closed reaction vessel (sealed reaction vessel) is preferable, and a closed reaction vessel is more preferable which has a volume 10 times to 100 times the volume of a mixture of the amino group-containing organic compound, the solvent, and the base.

(Other Step(s))

The method for producing a carbamic acid salt according to the present embodiment may include any optional step other than the reaction step. Examples of such any optional step include a purification step of increasing the purity of a carbamic acid salt. A purification method usually conducted in the organic synthesis field, such as filtration, adsorption, column chromatography, or distillation, can be adopted in the purification step. Specifically, when an objective carbamic acid salt is a solid, a product is collected by, for example, filtration after the reaction step, washed with a solvent which is the same in type as the solvent used in the reaction, and then dried in vacuum.

Hereinafter, the second aspect of the present invention will be described.

<B: 1. Method for Producing Carbamic Acid Ester>

A method for producing a carbamic acid ester according to one embodiment of the second aspect of the present invention includes a reaction step (hereinafter, sometimes abbreviated as "reaction step".) of producing a carbamic acid ester having a structure represented by the following formula (a-1) or (a-2), from a carbamic acid salt and a metal alkoxide.

(a-1)

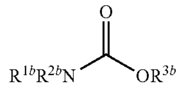

(a-2)

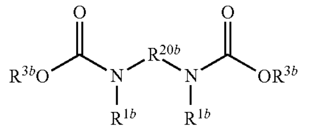

In the formulae, $R^{1b}$ each independently represents a hydrogen atom, or an unsubstituted or a substituted monovalent hydrocarbon group, $R^{2b}$ and $R^{3b}$ each independently represents an unsubstituted or a substituted monovalent hydrocarbon group, and $R^{20b}$ represents an unsubstituted or a substituted divalent hydrocarbon group.

Examples of such a reaction for producing the carbamic acid ester having the structure represented by the formula (a-1) or (a-2) from the carbamic acid salt and the metal alkoxide include the following reaction of benzylammonium N-benzylcarbamate and titanium tetramethoxide. The reaction mechanism in the reaction is presumed as follows.

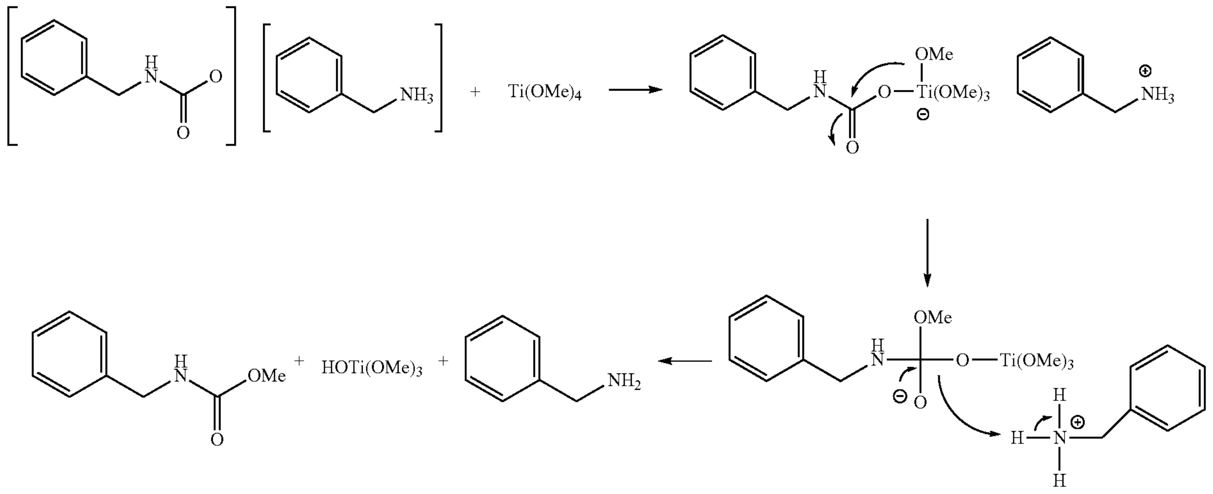

According to the present embodiment, a carbamic acid ester can be produced without neither sacrificial reagents, nor alkyl halides poor in environmental friendliness. As described below, according to the present embodiment, a carbamic acid salt can be produced with a low-concentration carbon dioxide mixed gas as a raw material, and a carbamic acid ester can be produced therefrom, and therefore, low-concentration carbon dioxide included in an exhaust gas or the like can be effectively utilized. Furthermore, a metal alkoxide reproducible by an alcohol is used in the present embodiment, and thus production of a carbamic acid ester can be realized where only low-concentration carbon dioxide, an amine, and an alcohol are substantially consumed and environmental friendliness is excellent.

<B: 1-1. Carbamic Acid Ester Having Structure Represented by Formula (a-1) or (a-2)>

The carbamic acid ester having the structure represented by the formula (a-1) or (a-2) is obtained by the production method according to the present embodiment.

($R_{1b}$)

$R^{1b}$ each independently represents a hydrogen atom, or an unsubstituted or a substituted monovalent hydrocarbon group.

The "hydrocarbon group" in the description of the second aspect of the present invention is not herein limited to a linear saturated hydrocarbon group, and may have each of a carbon-carbon unsaturated bond, a branched structure, and a cyclic structure.

The number of carbon atoms in $R^{1b}$ is not particularly limited, and is usually 1 or more, and usually 30 or less, preferably 24 or less, more preferably 20 or less.

Examples of the unsubstituted hydrocarbon group represented by $R^{1b}$ include an alkyl group such as an ethyl group, a n-propyl group, an iso-propyl group, a n-butyl group, a sec-butyl group, an iso-butyl group, a tert-butyl group, a n-pentyl group, an iso-pentyl group, a neopentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-docosyl group; a cycloalkyl group such as a cyclopropyl group, a cyclobutyl group, a cyclopentyl group and a cyclohexyl group; and an aromatic hydrocarbon group such as a phenyl group, a 1-naphthyl group, a 2-naphthyl group, a 1-phenanthryl group, a 2-phenanthryl group, a 3-phenanthryl group, a 4-phenanthryl group, a 9-phenanthryl group, a 1-anthryl group, a 2-anthryl group, a 9-anthryl group, a 1-pyrenyl group, a 2-pyrenyl group, a 4-pyrenyl group, a 1-triphenylenyl group and a 2-triphenylenyl group.

When the hydrocarbon group represented by $R^{1b}$ has a substituent, examples of the substituent include a deuterium atom; an alkyl group having 1 to 4 carbon atoms, such as a methyl group, an ethyl group, a n-propyl group, an isopropyl group, a n-butyl group, a sec-butyl group, an isobutyl group and a tert-butyl group; a cycloalkyl group having 3 to 4 carbon atoms, such as a cyclopropyl group and a cyclobutyl group; an aromatic hydrocarbon group having 6 to 10 carbon atoms, such as a phenyl group, a 1-naphthyl group and a 2-naphthyl group; a heterocyclic group, for example, an oxygen-containing heterocyclic group such as a furanyl group, a sulfur-containing heterocyclic group such as a thienyl group, and a nitrogen-containing heterocyclic ring group, such as a pyrrolyl group and a pyridyl group; a hydroxyl group; and an alkoxy group. Accordingly, when the hydrocarbon group represented by $R^{1b}$ has a substituent, examples of $R^{1b}$ can preferably include an aralkyl group such as a benzyl group, a phenethyl group, a 1-naphthylmethyl group and a 2-naphthylmethyl group; a cycloalkylalkyl group such as a cyclohexylmethyl group; a hydrocarbon group each having an oxygen-containing heterocyclic ring, such as a furfuryl group; a hydrocarbon group each having a sulfur-containing heterocyclic ring, such as a thienylmethyl group; and a hydrocarbon group each having a nitrogen-containing heterocyclic ring, such as a pyridylmethyl group, particularly preferably include a benzyl group.

When the hydrocarbon group has a substituent, the number of carbon atoms means the total number of carbon atoms of the number of carbon atoms in the substituent and the number of carbon atoms in the hydrocarbon group.

$R^{1b}$ is preferably hydrogen from the viewpoint of usefulness of a carbamic acid ester compound.

($R^{2b}$, $R^{3b}$)

$R^{2b}$ and $R^{3b}$ each independently represents an unsubstituted or a substituted monovalent hydrocarbon group.

The number of carbon atoms in $R^{2b}$ is not particularly limited, and is usually 1 or more, and usually 30 or less, preferably 24 or less, more preferably 20 or less.

The number of carbon atoms in $R^{3b}$ is not particularly limited, and is usually 1 or more, and usually 30 or less, preferably 24 or less, more preferably 20 or less.

Examples of each of the unsubstituted hydrocarbon groups represented by $R^{2b}$ and $R^{3b}$ include an alkyl group such as an ethyl group, a n-propyl group, an iso-propyl group, a n-butyl group, a sec-butyl group, an iso-butyl group, a tert-butyl group, a n-pentyl group, an iso-pentyl group, a neopentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-docosyl group; a cycloalkyl group such as a cyclopropyl group, a cyclobutyl group, a cyclopentyl group and a cyclohexyl group; and an aromatic hydrocarbon group such as a phenyl group, a 1-naphthyl group, a 2-naphthyl group, a 1-phenanthryl group, a 2-phenanthryl group, a 3-phenanthryl group, a 4-phenanthryl group, a 9-phenanthryl group, a 1-anthryl group, a 2-anthryl group, a 9-anthryl group, a 1-pyrenyl group, a 2-pyrenyl group, a 4-pyrenyl group, a 1-triphenylenyl group and a 2-triphenylenyl group.

When the hydrocarbon groups represented by $R^{2b}$ and $R^{3b}$ each has a substituent, examples of the substituent include a deuterium atom; an alkyl group having 1 to 4 carbon atoms, such as a methyl group, an ethyl group, a n-propyl group, an isopropyl group, a n-butyl group, a sec-butyl group, an isobutyl group and a tert-butyl group; a cycloalkyl group having 3 to 4 carbon atoms, such as a cyclopropyl group and a cyclobutyl group; an aromatic hydrocarbon group having 6 to 10 carbon atoms, such as a phenyl group, a 1-naphthyl group and a 2-naphthyl group; a heterocyclic group, for example, an oxygen-containing heterocyclic group such as a furanyl group, a sulfur-containing heterocyclic group such as a thienyl group, and a nitrogen-containing heterocyclic ring group, such as a pyrrolyl group and a pyridyl group. Accordingly, when the hydrocarbon groups represented by $R^{2b}$ and $R^{3b}$ each has a substituent, examples of $R^{2b}$ and $R^{3b}$ can preferably include an aralkyl group such as a benzyl group, a phenethyl group, a 1-naphthylmethyl group and a 2-naphthylmethyl group; a cycloalkylalkyl group such as a cyclohexylmethyl group; a hydrocarbon group each having an oxygen-containing heterocyclic ring, such as a furfuryl group; a hydrocarbon group each having a sulfur-containing heterocyclic ring, such as a thienylmethyl group; and a hydrocarbon group each having a nitrogen-containing heterocyclic ring, such as a pyridylmethyl group, particularly preferably include a benzyl group.

When the hydrocarbon group is a branched alkyl group, the number of carbon atoms in the hydrocarbon group is defined as the number of carbon atoms in a main chain. When the hydrocarbon group has a substituent, the number of carbon atoms in the substituent is not included in the number of carbon atoms in the hydrocarbon group.

$R^{2b}$ is preferably an alkyl group such as a n-hexyl group; a cycloalkyl group such as a cyclohexyl group; an aromatic hydrocarbon group such as a phenyl group; or an aralkyl group such as a benzyl group; more preferably a benzyl group, a n-hexyl group, a cyclohexyl group, or a phenyl group, further preferably a benzyl group or a phenyl group, from the viewpoint of availability of raw materials.

$R^{3b}$ is preferably an alkyl group, more preferably a methyl group, an ethyl group, a n-propyl group, or a n-butyl group, from the viewpoint of availability of raw materials.

($R^{20b}$)

$R^{20b}$ represents an unsubstituted or a substituted divalent hydrocarbon group.

Examples of the divalent hydrocarbon group include a methylene group; an ethylene group; a linear, branched or cyclic alkylene group having 3 or more carbon atoms; or an arylene group having 6 or more carbon atoms.

The number of carbon atoms in the divalent hydrocarbon group is not particularly limited, and is preferably 2 or more, and preferably 10 or less, more preferably 7 or less. The divalent hydrocarbon group hay have an unsaturated bond. When the divalent hydrocarbon group has a substituent, the number of carbon atoms in the divalent hydrocarbon group means the number of carbon atoms also including the number of carbon atoms in the substituent. Examples of the substituent include those exemplified in the description in the section ($R^{1b}$).

Specific examples of $R^{20b}$ include a linear hydrocarbon group such as a methylene group, an ethylene group, a tetramethylethylene group, a n-propylene group (trimethylene group), a 1-methylpropylene group, a 1,1-dimethylpropylene group, a 2-methylpropylene group, a 1,2-dimethylpropylene group, a 2,2-dimethylpropylene group, a 1,1,2-trimethylpropylene group, a 1,1,3-trimethylpropylene group, a n-butylene group (tetramethylene group), a 2-methyl-1,4-butylene group, a 3-methyl-1,4-butylene group, a 2,2-dimethyl-1,4-butylene group, a 2,3-dimethyl-1,4-butylene group, a 2,2,3-trimethyl-1,4-butylene group, a n-pentylene group (pentamethylene group) and a n-hexanylene group (hexamethylene group); an alicyclic hydrocarbon group such as a 1,4-cyclohexylene group; a 1,4-phenylene group, a 1,2-phenylene group and a 1,3-phenylene group, each obtained by removal of two hydrogen atoms from a benzene ring; an aromatic hydrocarbon group such as a dimethylphenylene group (xylyl group) obtained by removal of two hydrogen atoms from a benzene ring of xylene, a methylphenylene group (tolylene group) obtained by removal of two hydrogen atoms from a benzene ring of toluene, and a naphthanylene group obtained by removal of two hydrogen atoms from naphthalene; and a divalent group including an aliphatic hydrocarbon group and an aromatic hydrocarbon group, such as a 1,4-phenylenebis(methylene) group, a 1,4-phenylenebis(ethylene) group, a group obtained by removal of one hydrogen atom from each of two benzene rings of biphenyl, and a group obtained by removal of one hydrogen atom from each of two benzene rings of diphenylmethane.

Examples of the carbamic acid ester represented by the formula (a-1) or (a-2) include the following compounds.

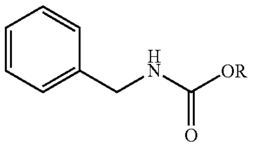

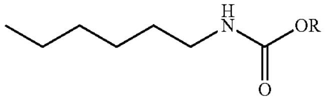

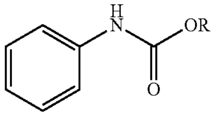

-continued

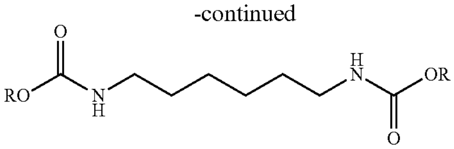

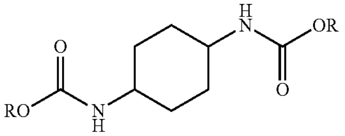

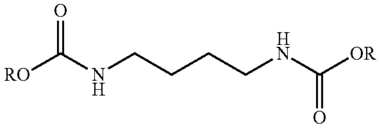

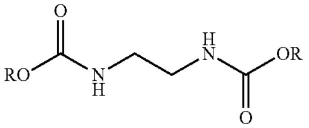

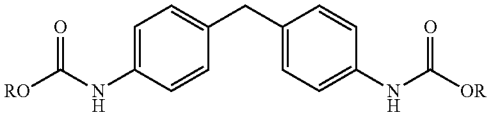

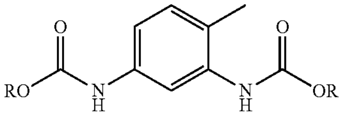

R = Me, Et, $^n$Pr, $^i$Pr, $^n$Bu, $^i$Bu, $^t$Bu, Hex

<B: 1-2. Carbamic Acid Salt>

The carbamic acid salt for use in the present embodiment may be one that can produce the carbamate represented by the formula (a-1) or (a-2). In other words, the carbamic acid salt may be any carbamic acid salt which contains a hydrogen atom or an unsubstituted or a substituted monovalent hydrocarbon group $R^{1b}$ and also contains an unsubstituted or a substituted monovalent hydrocarbon group $R^{2b}$ or any carbamic acid salt which contains an unsubstituted or a substituted monovalent hydrocarbon group $R^{1b}$ and also contains an unsubstituted or a substituted divalent hydrocarbon group $R^{20b}$. Preferable examples include a carbamic acid salt represented by formula (B-1) or formula (B-2) described below.

The carbamic acid salt here used may be a commercially available product purchased or may be synthesized. When the carbamic acid salt is synthesized, the production method thereof is not particularly limited, and the carbamic acid salt can be produced by, for example, the method for producing a carbamic acid salt according to the first aspect of the present invention. Alternatively, one can be used which is produced by a reaction of an amino group-containing organic compound having one or more primary or secondary amino groups, more specifically an aliphatic monoamine such as benzylamine or hexylamine, or an aliphatic diamine such as ethylenediamine, with carbon dioxide. The carbon dioxide for use in the reaction can be a pure carbon dioxide gas, or can also be a mixed gas containing carbon dioxide at a partial pressure of at 1 atm or less, for example, a mixed gas having a content rate of carbon dioxide of 0.01% or more in terms of volume ratio.

In the present embodiment, it is preferable to further include a carbamic acid salt production step of contacting an amino group-containing organic compound with a carbon dioxide-containing mixed gas in a solvent to produce the carbamic acid salt. The volume of carbon dioxide in the carbon dioxide-containing mixed gas is usually 0.01% or more, preferably 1% or more, more preferably 10% or more, further preferably 15% or more, particularly preferably 20% or more, and preferably 50% or less. The solvent for use in the carbamic acid salt production step is not particularly limited, and a hydrocarbon-based solvent such as hexane, benzene, or toluene can be preferably used. The reaction time may be appropriately adjusted depending on the partial pressure of carbon dioxide in the carbon dioxide-containing mixed gas, and the reaction scale. For example, when the volume of carbon dioxide in the carbon dioxide-containing mixed gas is 15%, 1 mmol of the amino group-containing organic compound as a raw material can be reacted for 5 minutes or more and 10 minutes or less to synthesize a carbamic acid salt at a yield of 80% or more. When 40 mmol of the amino group-containing organic compound is used, a yield of 90% or more can be achieved by a reaction time of about 180 minutes. Such a carbamic acid salt generated can be easily isolated by filtration.

The present inventors have confirmed that the carbamic acid salt can be produced at a high yield of, for example, 99% or more by a reaction shown by the following scheme in the carbamic acid salt production step. The carbamic acid salt can also be obtained at a high yield of isolation of 93% even in synthesis using a mixed gas of low partial pressure carbon dioxide.

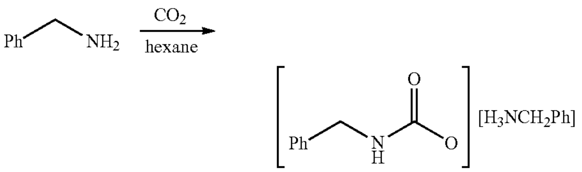

While a method for producing a carbamic acid ester with carbon dioxide as a raw material has been heretofore reported, all such methods have required a sacrificial reagent or an alkyl halide poor in environmental friendliness. In this regard, the production method of the present embodiment not only uses neither any sacrificial reagent, nor any alkyl halide, but also can use a mixed gas where carbon dioxide is at a low partial pressure. For example, an exhaust gas in a thermal power plant usually includes about 15% of carbon dioxide. The method for producing a carbamic acid ester including production of production of a carbamic acid salt using a low-concentration carbon dioxide-containing mixed gas enables effective utilization of low-concentration carbon dioxide, namely, the method is effective for reduction of greenhouse gas emissions and is excellent in environmental friendliness.

<B: 1-3. Metal Alkoxide>

The metal alkoxide for use in the present embodiment may be one that can produce the carbamic acid ester represented by formula (a-1) or (a-2). In other words, the metal alkoxide may be any metal alkoxide containing an alkoxide group —$OR^{3b}$. Preferable examples include a metal alkoxide represented by formula (C-1) or (C-2) described below. The metal alkoxide here used may be a commercially available product purchased or may be synthesized.

The metal alkoxide is a reaction agent reproducible by an alcohol. After the reaction step, the residue are collected from a reaction product and then the metal alkoxide can be reproduced using an alcohol. The metal alkoxide, which is reproduced, can also be reused in the reaction step. Accordingly, the present embodiment can produce a carbamic acid salt with a low-concentration carbon dioxide, and can provide a method for producing a carbamic acid ester, where only low-concentration carbon dioxide, an amine, and an alcohol are substantially consumed and environmental friendliness is excellent.

<B: 1-4. Method for Producing Carbamic Acid Ester Represented by Formula (A-1)>

In the present embodiment, preferably, the carbamic acid salt is a carbamic acid salt represented by formula (B-1), the metal alkoxide is a metal alkoxide represented by formula (C-1), and the carbamic acid ester having the structure represented by the formula (a-1) is a carbamic acid ester represented by formula (A-1).

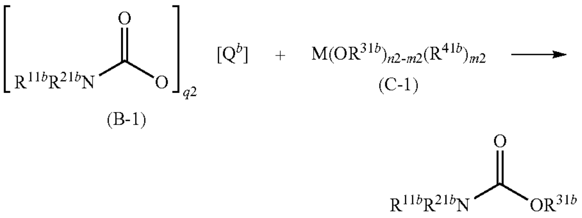
(B-1) (C-1) (A-1)

In the formulae, $R^{11b}$ represents a hydrogen atom, an unsubstituted or a substituted monovalent hydrocarbon group; $R^{21b}$ and $R^{31b}$ each independently represents an unsubstituted or a substituted monovalent hydrocarbon group; $R^{41b}$ each independently represents an unsubstituted or a substituted hydrocarbon ligand, an unsubstituted or a substituted alkoxy ligands, amide ligands, and halide ligands different from —$OR^{31b}$; M represents a metal atom or a semimetal atom; n2 represents the oxidation number of M and (n2−m2) is an integer of 1 to 6; m2 represents an integer of 0 or more and (n2−1) or less; $Q^b$ represents a q2-valent counter cation; and q2 is 1 or 2.

<B: 1-4-1. Carbamic Acid Ester Represented by Formula (A-1)>

In the formula (A-1), $R^{11b}$ represents a hydrogen atom, an unsubstituted or a substituted monovalent hydrocarbon group; and $R^{21b}$ and $R^{31b}$ each independently represents an unsubstituted or a substituted monovalent hydrocarbon group.

The detail of $R^{11b}$ is applied by the above description about $R^{1b}$.

The detail of $R^{21b}$ is applied by the above description about $R^{2b}$.

The detail of $R^{31b}$ is applied by the above description about $R^{3b}$.

<B: 1-4-2. Carbamic Acid Salt Represented by Formula (B-1)>

In the formula (B-1), $R^{11b}$ represents a hydrogen atom, or an unsubstituted or a substituted monovalent hydrocarbon group, $R^{21b}$ and $R^{31b}$ each independently represents an unsubstituted or a substituted monovalent hydrocarbon group, and $Q^b$ represents a counter cation.

$R^{11b}$ in the formula (B-1) corresponds to $R^{11b}$ in the formula (A-1). $R^{21b}$ in the formula (B-1) corresponds to $R^{21b}$ in the formula (A-1). $R^{31b}$ in the formula (B-1) corresponds to $R^{31b}$ in the formula (A-1). Accordingly, the detail of $R^{11b}$ is applied by the above description about $R^{1b}$. The detail of $R^{21b}$ is applied by the above description about $R^{2b}$. The detail of $R^{31b}$ is applied by the above description about $R^{3b}$.

($Q^b$)

$Q^b$ represents a counter cation in the carbamic acid salt and is not particularly limited as long as it represents a monovalent or divalent cation, and examples thereof include an ammonium cation, an amidinium cation, a guanidinium cation, a phosphonium cation, a phosphazenium cation, a carbocation, a sulfonium cation, an iodonium cation, an alkali metal cation, and an alkaline earth metal cation.

Examples of the ammonium cation include a primary ammonium cation such as a n-butylammonium cation; a secondary ammonium cation such as a diethylammonium cation; a tertiary ammonium cation such as a triethylammonium cation; and a quaternary ammonium cation such as a tetramethylammonium cation, a phenyltrimethylammonium cation and a tetrabutylammonium cation.

Examples of the amidinium cation include a formamidinium cation, an acetamidinium cation, a 1,5-diazabicyclo[4.3.0]non-5-enium cation, and a 1,8-diazabicyclo[5.4.0]undec-7-enium cation respectively obtained by protonation of formamidine, acetamidine, 1,5-diazabicyclo[4.3.0]non-5-ene, and 1,8-diazabicyclo[5.4.0]undec-7-ene, as well as derivatives thereof each having one or more substituents. Examples of such a substituent include hydrocarbon groups such as alkyl groups, cycloalkyl groups, and aromatic hydrocarbon groups, exemplified in the description of the section ($R^{1b}$).

Examples of the guanidinium cation include a 1,1,3,3-tetramethyl guanidinium cation, a 2-tert-butyl-1,1,3,3-tetramethyl guanidinium cation, a 1,5,7-triazabicyclo[4.4.0]dec-5-enium cation, and a 7-methyl-1,5,7-triazabicyclo[4.4.0]dec-5-enium cation respectively obtained by protonation of 1,1,3,3-tetramethylguanidine, 2-tert-butyl-1,1,3,3-tetramethylguanidine, 1,5,7-triazabicyclo[4.4.0]dec-5-ene, and 7-methyl-1,5,7-triazabicyclo[4.4.0]dec-5-ene, as well as derivatives thereof each having one or more substituents. Examples of such a substituent include hydrocarbon groups such as alkyl groups, cycloalkyl groups, and aromatic hydrocarbon groups, exemplified in the description of the section ($R^{1b}$).

Examples of the phosphonium cation include a tertiary phosphonium cation such as a triphenyl phosphonium cation and a tri-tert-butyl phosphonium cation; and a quaternary phosphonium cation such as a tetraphenyl phosphonium cation, a tetra-p-tolyl phosphonium cation, a triphenylbenzyl phosphonium cation, a triphenylbutyl cation, a tetraethylphosphonium cation and a tetrabutylphosphonium cation.

Examples of the phosphazenium cation include a tert-butylimino-tris(dimethylamino)phosphoranium cation, a tert-butylimino-tri(pyrrolidino)phosphoranium cation, a 2-tert-butylimino-2-diethylamino-1,3-dimethylperhydro-1,3,2-diazaphosphorinium cation, a 1-tert-butyl-2,2,4,4,4-pentakis(dimethylamino)-2$\lambda^5$,4$\lambda^5$-catenadi(phosphazenium), and a 1-tert-butyl-4,4,4-tris(dimethylamino)-2,2-bis[tris(dimethylamino)phosphoranylideneamino]-2$\lambda^5$,4$\lambda^5$-catenadi(phosphazenium) cation respectively obtained by protonation of tert-butylimino-tris(dimethylamino)phosphorane, tert-butylimino-tri(pyrrolidino)phosphorane, 2-tert-butylimino-2-diethylamino-1,3-dimethylperhydro-1,3,2-diazaphosphorine, 1-tert-butyl-2,2,4,4,4-pentakis(dimethylamino)-2$\lambda^5$,4$\lambda^5$-catenadi(phosphazene), and 1-tert-butyl-4,4,4-tris(dimethylamino)-2,2-bis[tris(dimethylamino)phosphoranylideneamino]-2$\lambda^5$,4$\lambda^5$-catenadi(phosphazene), as well as derivatives thereof each having one or more substituents. Examples of such a substituent include hydrocarbon groups such as alkyl groups, cycloalkyl groups, and aromatic hydrocarbon groups, exemplified in the description of the section (Rib) Examples of the carbocation include monovalent carbocations such as a triphenylmethyl cation, a tropylium cation, and an azulenium cation.

Examples of the sulfonium cation include a triphenylsulfonium cation, a 4-(phenylthio)phenyldiphenylsulfonium cation, bis[4-(diphenylsulfonio)phenyl]sulfide, and a 4-hydroxyphenylmethylbenzylsulfonium cation.

Examples of the iodonium cation include a diphenyliodonium cation, a di-p-tolyliodonium cation, and a 4-isopropylphenyl(p-tolyl)iodonium cation.

Examples of the alkali metal cation include a lithium cation, a sodium cation, and a potassium cation.

Examples of the alkaline earth metal cation include a magnesium cation and a calcium cation.

An ammonium cation, an amidinium cation, a guanidinium cation, a phosphonium cation, a phosphazenium cation, a carbocation, an alkali metal cation, or an alkaline earth metal cation is preferable, and an ammonium cation or an amidinium cation is more preferable, from the viewpoint of ease of synthesis. In particular, a primary ammonium cation, a tertiary ammonium cation, or a 1,8-diazabicyclo[5.4.0]undec-7-enium cation is preferable.

(q2)

q2 is 1 or 2. q2 represents the number of carbamic anions, and is a value equal to the valence of $Q^b$. Accordingly, when $Q^b$ is a monovalent cation, q2 is 1, and when $Q^b$ is a divalent cation, q2 is 2.

Specific examples of the carbamic acid salt represented by the formula (B-1) include methylammonium N-methylcarbamate, ethylammonium N-ethylcarbamate, propylammonium N-propylcarbamate, butylammonium N-butylcarbamate, pentylammonium N-pentylcarbamate, hexylammonium N-hexylcarbamate, benzylammonium N-benzylcarbamate, phenylammonium N-phenylcarbamate, and a compound represented by the following formula, and an amidinium salt, a guanidinium salt, a phosphonium salt, a phosphazenium salt, a carbocation salt, an alkali metal salt, or an alkaline earth metal salt thereof in which each counter cation is, respectively, an amidinium cation other than a 1,8-diazabicyclo[5.4.0]undec-7-enium cation, a guanidinium cation, a phosphonium cation, a phosphazenium cation, a carbocation, an alkali metal cation, or an alkaline earth metal cation, but are not limited thereto.

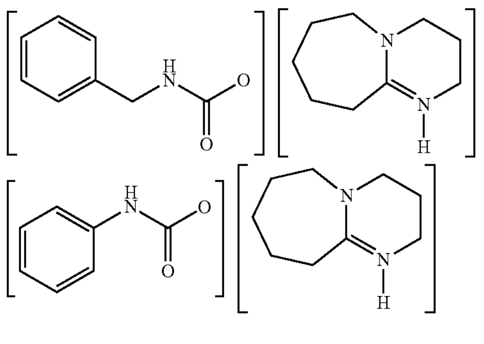

<B: 1-4-3. Metal Alkoxide Represented by Formula (C-1)>

In the formula (C-1), $R^{31b}$ represents an unsubstituted or a substituted monovalent hydrocarbon group; $R^{41b}$ each independently represents an unsubstituted or a substituted hydrocarbon ligand an unsubstituted or a substituted alkoxy ligands, amide ligands, and halide ligands different from —$OR^{31b}$; M represents a metal atom or a semimetal atom; n2 represents the oxidation number of M and (n2−m2) is an integer of 1 to 6; and m2 represents an integer of 0 or more and (n2−1) or less.

(M)

M represents a metal atom or a semimetal atom.

Each of the metal atom and the semimetal atom is not particularly limited in terms of type thereof, and examples include metal atoms or semimetal atoms, selected from the group consisting of silicon, titanium, zirconium, germanium, indium, tin, tantalum, zinc and tungsten. In particular, silicon and titanium are preferable from the viewpoint of availability.

($R^{31b}$)

$R^{31b}$ represents an unsubstituted or a substituted monovalent hydrocarbon group.

$R^{31b}$ in the formula (C-1) corresponds to $R^{31b}$ in the formula (A-1). Accordingly, the detail of $R^{31b}$ is applied by the above description about $R^{3b}$.

($R^{41b}$)

$R^{41b}$ each independently represents an unsubstituted or a substituted hydrocarbon ligand, an unsubstituted or a substituted alkoxy ligands, amide ligands, and halide ligands different from —$OR^{31b}$.

Examples of the unsubstituted hydrocarbon ligand includes alkyl ligands such as a methyl ligand and an ethyl ligand; cycloalkyl ligands such as a cyclohexyl ligand; aryl ligands such as a phenyl ligand, a naphthyl ligand, a cyclopentadienyl ligand, a cyclohexadienyl ligand, a cyclooctadienyl ligand, a cyclooctatetraenyl ligand, and a norbomadienyl ligand; and aralkyl ligands such as a benzyl ligand, a methylcyclopentadienyl ligand, a methylcyclohexadienyl ligand, a methylcyclooctadienyl ligand, and a methylcyclooctatetraenyl ligand. Examples of the substituent which the hydrocarbon ligand may have include a hydroxy group, an ester group (—COOR), an amide group (—CONRR'), a halogen atom, an alkylthio group (—SR), an amino group (—NRR'), a carboxy group, a nitro group, a sulfonic acid group (—$SO_3H$), an oxygen-containing heterocyclic group such as a furanyl group, a sulfur-containing heterocyclic group such as a thienyl group, and a nitrogen-containing heterocyclic group such as a pyridyl group.

Examples of the unsubstituted alkoxy ligand different from —$OR^{31b}$ include a methoxy ligand, an ethoxy ligand, a propoxy ligand, a butoxy ligand, a pentoxy ligand, a dodecyloxy ligand, and a phenoxy ligand. Examples of the substituent with which the alkoxy ligand may have include a hydroxy group, an ester group (—COOR), an amide group (—CONRR'), a halogen atom, an alkylthio group (—SR), an amino group (—NRR'), a carboxy group, a nitro group, a sulfonic acid group (—$SO_3H$), an oxygen-containing heterocyclic group such as a furanyl group, a sulfur-containing heterocyclic group such as a thienyl group, and a nitrogen-containing heterocyclic group such as a pyridyl group.

Examples of the amide ligand include an unsubstituted amide ligand ($NH_2$), a methylamide ligand (NHMe), a dimethylamide ligand ($NMe_2$), a diethylamide ligand ($NEt_2$), a di-n-propylamide ligand ($NPr_2$), an isopropylamide ligand, a di-n-butylamide ligand, and a di-t-butylamide ligand.

Examples of the halide ligand include a fluorine ligand, a chlorine ligand, a bromine ligand, and an iodine ligand.

When m2 is 2 to 5, a plurality of $R^{41b}$(s) may be the same as each other or different from each other, and all $R^{41b}$(s) are preferably the same as each other with from the viewpoint of availability.

(n2)

n2 represents the oxidation number of M, and (n2−m2) is an integer of 1 to 6.

(m2)

m2 represents an integer of 0 or more and (n2−1) or less. In other words, it is an integer of 0 to 5.

Specific examples of the metal alkoxide represented by formula (C-1) include alkoxysilanes such as tetramethoxysilane, tetraethoxysilane, tetra(n-propoxy)silane, tetra(iso-propoxy)silane, tetra(n-butoxy)silane, tetra(2-butoxy)silane, tetra(t-butoxy)silane, trimethoxy(iso-propoxy)silane, trimethoxy(n-butoxy)silane, trimethoxy(2-butoxy)silane, trimethoxy(t-butoxy)silane, trimethoxysilane, triethoxysilane, methyltrimethoxysilane, methyltriethoxysilane, methyltripropoxysilane, ethyltrimethoxysilane, ethyltriethoxysilane, ethyltripropoxysilane, propyltrimethoxysilane, propyltriethoxysilane, propyltrimethoxysilane, cyclohexyltrimethoxysilane, cyclohexyltriethoxysilane, cyclohexyltripropoxysilane, phenyltrimethoxysilane, phenyltriethoxysilane, phenyltripropoxysilane, vinyltrimethoxysilane, vinyltriethoxysilane, vinyltripropoxysilane, dimethoxydimethylsilane, diethoxydimethylsilane, dimethoxydiethylsilane, diethoxydiethylsilane, dimethoxymethylvinylsilane, dimethoxydiphenylsilane, dimethoxymethylphenylsilane and N-(2-aminoethyl)-3-aminopropyltrimethoxysilane;

titanium alkoxides such as titanium tetramethoxide, titanium tetraethoxide, titanium tetraallyloxide, titanium tetra-n-propoxide, titanium tetra-iso-propoxide, titanium tetra-n-butoxide, tetraisobutoxide, titanium tetra-sec-butoxide, titanium tetra-t-butoxide titanium, tetra-n-pentyloxide, titanium tetracyclopentyloxide, titanium tetrahexyloxide, titanium tetracyclohexyloxide, titanium tetrabenzyloxide, titanium tetraoctyloxide, titanium tetrakis(2-ethylhexyloxide), titanium tetradecyloxide, titanium tetradodecyloxide, titanium tetrastearyloxide, titanium tetrakis(8-hydroxyoctyloxide), titanium diisopropoxybis(2-ethyl-1,3-hexanediolate), titanium bis(2-ethylhexyloxy)bis(2-ethyl-1,3-hexanediolate), titanium tetrakis(2-chloroethoxide), titanium tetrakis(2-bromoethoxide), titanium tetrakis (2-methoxyethoxide), titanium tetrakis(2-ethoxyethoxide), titanium butoxide trimethoxide, titanium dibutoxide dimethoxide, titanium butoxide triethoxide, titanium dibutoxide diethoxide, titanium butoxide triisopropoxide, titanium dibutoxide diisopropoxide, titanium tetraphenoxide, titanium tetrakis(o-chlorophenoxide), titanium tetrakis(m-nitrophenoxide), titanium tetrakis(p-methylphenoxide), titanium tetrakis(trimethylsilyloxide), titanium triethoxide, titanium trimethoxide, titanium triisopropoxide, titanium tributoxide, titanium methyldimethoxide, titanium ethyltriethoxide, titanium methyltriisopropoxide, tetradimethylaminotitanium, dimethyltitanium diacetylacetonate and ethyltitanium triacetylacetonate;

zirconium alkoxides such as zirconium tetramethoxide, zirconium tetraethoxide, zirconium tetraallyloxide, zirconium tetra-n-propoxide, zirconium tetraisopropoxide, zirconium tetra-n-butoxide, zirconium tetraisobutoxide, zirconium tetra-sec-butoxide, zirconium tetra-t-butoxide, zirconium tetra-n-pentyloxide, zirconium tetracyclopentyloxide, zirconium tetrahexyloxide, zirconium tetracyclohexyloxide, zirconium tetrabenzyloxide, zirconium tetraoctyloxide, zirconium tetrakis (2-ethylhexyloxide), zirconium tetradecyloxide, zirconium tetradodecyloxide, zirconium tetrastearyloxide, zirconium tetrakis(8-hydroxyoctyloxide), zirconium diisopropoxybis(2-ethyl-1,3-hexanediolate), zirconium bis(2-ethylhexyloxy)bis(2-ethyl-1,3-hexanediolate), zirconium tetrakis(2-chloroethoxide), zirconium tetrakis(2-bromoethoxide), zirconium tetrakis(2-methoxyethoxide), zirconium tetrakis(2-ethoxyethoxide), zirconium butoxide trimethoxide, zirconium dibutoxide dimethoxide, zirconium butoxide triethoxide, zirconium dibutoxide diethoxide, zirconium butoxide triisopropoxide, zirconium dibutoxide diisopropoxide, zirconium tetraphenoxide, zirconium tetrakis(o-chlorophenoxide), zirconium tetrakis(m-nitrophenoxide) and zirconium tetrakis(p-methylphenoxide);

germanium alkoxides such as germanium tetraethoxide, germanium tetra propoxide, germanium tetraisopropoxide, germanium tetra(n-butoxide), germanium tetra (2-butoxide) and germanium tetra(t-butoxide);

indium alkoxides such as indium tetra(n-butoxide), indium tetra(2-butoxide), indium tetra(t-butoxide), indium trimethoxide, indium triethoxide, indium tri(n-propoxide), indium triisopropoxide, indium tri(n-butoxide), indium triisobutoxide, indium tri(t-butoxide) and indium tri(s-butoxide);

tin alkoxides such as dibutyltin dimethoxide, dibutyltin diethoxide and dibutyltin dipropoxide;

tantalum alkoxides such as tantalum tetramethoxide, tantalum tetraethoxide, tantalum tetra(n-propoxy), tantalum tetraisopropoxide, tantalum tetra(n-butoxide), tantalum tetra(2-butoxide), tantalum tetra(t-butoxide) and tantalum pentaethoxide;

zinc alkoxides such as zinc isopropoxide, zinc tetra(n-butoxide), zinc tetra(2-butoxide) and zinc tetra(t-butoxide); and tungsten alkoxides such as tungsten pentamethoxide, tungsten pentaethoxide, tungsten pentaisopropoxide, tungsten(V) pentabutoxide, tungsten triisobutoxide and tungsten tri(t-butoxide)tungsten.

The metal alkoxide represented by formula (C-1) is preferably at least one selected from the group consisting of a titanium compound and a silicon compound, more preferably titanium tetramethoxide, titanium tetra-iso-propoxide, titanium tetra-n-butoxide, titanium tetra-t-butoxide, tetramethoxysilane, tetraethoxysilane, tetra-n-propoxysilane, or tetra-n-butoxysilane, further preferably titanium tetramethoxide, titanium tetra-iso-propoxide, titanium tetra-n-butoxide, titanium tetra-t-butoxide, or tetramethoxysilane, from the viewpoint of availability.

In the present embodiment, a metal alkoxide compound may be charged into a reaction system, or the metal alkoxide may be generated in a reaction system. Examples include a method for generating tetraethoxy zirconium by a reaction of zirconium tetrachloride ($ZrCl_4$) with sodium ethoxide. Examples include a method for generating zirconocene diethoxide by a reaction of zirconocene dichloride ($Cp_2ZrCl_2$) with sodium ethoxide. Examples include a method for generating dibutyltin diethoxide by a reaction of dibutyltin dichloride ($Bu_2SnCl_2$) with sodium ethoxide.

<B: 1-5. Method for Producing Carbamic Acid Ester Represented by Formula (A-2)>

In the present embodiment, preferably, the carbamic acid salt is a carbamic acid salt represented by formula (B-2), the metal alkoxide is a metal alkoxide represented by formula (C-2), and the carbamic acid ester having the structure represented by the formula (a-2) is a carbamic acid ester represented by formula (A-2).

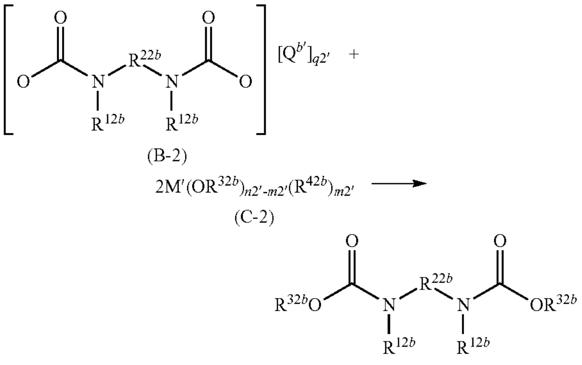

(B-2) (C-2) (A-2)

In the formulae, $R^{12b}$ each independently represents a hydrogen atom, or an unsubstituted or a substituted monovalent hydrocarbon group; $R^{22b}$ represents an unsubstituted or a substituted divalent hydrocarbon group; $R^{32b}$ each independently represents an unsubstituted or a substituted monovalent hydrocarbon group; $R^{42b}$ each independently represents an unsubstituted or a substituted hydrocarbon ligand, an unsubstituted or a substituted alkoxy ligands, amide ligands, and halide ligands different from $-OR^{32b}$; M' represents a metal atom or a semimetal atom; n2' represents the oxidation number of M' and (n2'−m2') is an integer of 1 to 6; m2' represents an integer of 0 or more and (n2'−1) or less; $Q^{b'}$ represents a (2/q2')-valent counter cation; and q2' is 1 or 2.

<B: 1-5-1. Carbamic Acid Ester Represented by Formula (A-2)>

In the formula (A-2), $R^{12b}$ each independently represents a hydrogen atom, or an unsubstituted or a substituted monovalent hydrocarbon group; $R^{22b}$ represents an unsubstituted or a substituted divalent hydrocarbon group; and $R^{32b}$ each independently represents an unsubstituted or a substituted monovalent hydrocarbon group.

The detail of $R^{12b}$ is applied by the above description about $R^{1b}$.

The detail of $R^{22b}$ is applied by the above description about $R^{20b}$.

The detail of $R^{32b}$ is applied by the above description about $R^{3b}$.

<B: 1-5-2. Carbamic Acid Salt Represented by Formula (B-2)>

In the formula (B-2), $R^{12b}$ each independently represents a hydrogen atom, or an unsubstituted or a substituted monovalent hydrocarbon group; $R^{22b}$ represents an unsubstituted or a substituted divalent hydrocarbon group; and $Q^{b'}$ represents a counter cation.

$R^{12b}$ in the formula (B-2) corresponds to $R^{12b}$ in the formula (A-2). $R^{22b}$ in the formula (B-2) corresponds to $R^{22b}$ in the formula (A-2). Accordingly, the detail of $R^{12b}$ is applied by the above description about $R^{1b}$. The detail of $R^{22b}$ is applied by the above description about $R^{2b}$.

($Q^{b'}$)

$Q^{b'}$ represents a counter cation in the carbamic acid salt, and is not particularly limited as long as it is a monovalent or divalent cation, and examples thereof include an ammonium cation, an amidinium cation, a guanidinium cation, a phosphonium cation, a phosphazenium cation, a carbocation, a sulfonium cation, an iodonium cation, an alkali metal cation, and an alkaline earth metal cation. Specific examples of such a cation include those described above in the section of ($Q^b$).

An ammonium cation, an amidinium cation, a guanidinium cation, a phosphonium cation, a phosphazenium cation, a carbocation, an alkali metal cation, or an alkaline earth metal cation is preferable, and an ammonium cation, an amidinium cation, a guanidinium cation, or a phosphazenium cation is more preferable, from the viewpoint of ease of synthesis. In particular, a tert-butylimino-tri(pyrrolidino) phosphoranium cation or a 1,8-diazabicyclo[5.4.0]undec-7-enium cation is preferable.

(q2')

q2' is 1 or 2. (2/q2') represents the number of counter cation $Q^b$(s), and, namely, when $Q^b$ represents a monovalent cation, q2' is 2, and when $Q^b$ represents a divalent cation, q2' is 1.

Specific examples of the carbamic acid salt represented by the formula (B-2) include a compound represented by the following formula, and an amidinium salt, a guanidinium salt, a phosphonium salt, a phosphazenium salt, a carbocation salt, an alkali metal salt, or an alkaline earth metal salt thereof in which each counter cation is, respectively, an amidinium cation other than a 1,8-diazabicyclo[5.4.0]undec-7-enium cation, a guanidinium cation, a phosphonium cation, a phosphazenium cation, a carbocation, an alkali metal cation, or an alkaline earth metal cation.

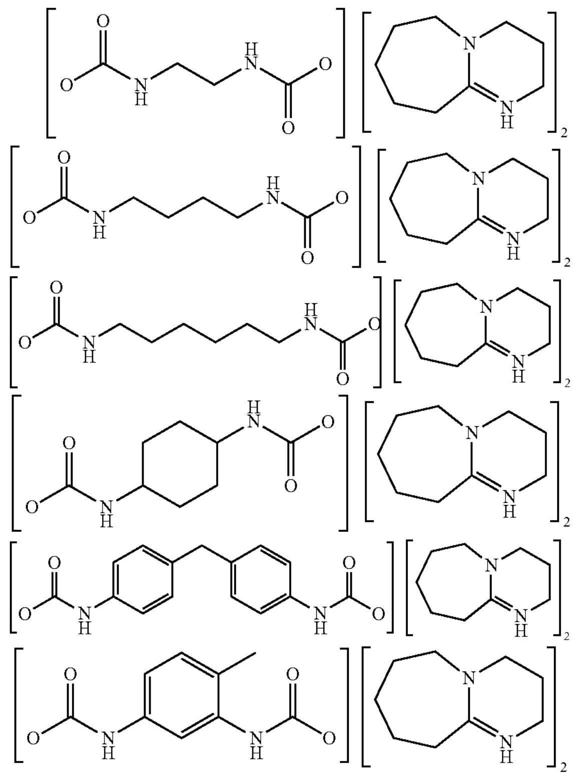

Specific examples of the carbamic acid salt represented by the formula (B-2) also include a compound represented by the following formula, and an amidinium salt, a guanidinium salt, a phosphonium salt, a phosphazenium salt, a carbocation salt, an alkali metal salt, or an alkaline earth metal salt thereof in which each counter cation is, respectively, an amidinium cation, a guanidinium cation, a phosphonium cation, a phosphazenium cation other than tert-butylimino-tri(pyrrolidino)phosphoranium cation, a carbocation, an alkali metal cation, or an alkaline earth metal cation, but are not limited thereto.

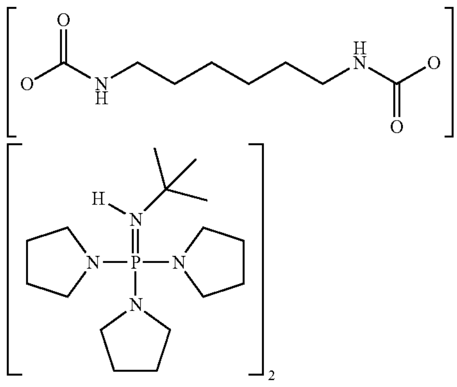

<B: 1-5-3. Metal Alkoxide Represented by Formula (C-2)>

In the formula (C-2), $R^{32b}$ represents an unsubstituted or a substituted monovalent hydrocarbon group; $R^{42b}$ each independently represents an unsubstituted or a substituted hydrocarbon ligand, an unsubstituted or a substituted alkoxy ligands, amide ligands, and halide ligands different from —$OR^{32b}$; M' represents a metal atom or a semimetal atom; n2' represents the oxidation number of M' and (n2'−m2') is an integer of 1 to 6; and m2' represents an integer of 0 or more and (n2'−1) or less.

(M')

M' represents a metal atom or a semimetal atom.

The metal atom and the semimetal atom are each not particularly limited in terms of type thereof, and examples include metal atoms or semimetal atoms selected from the group consisting of silicon, titanium, zirconium, germanium, indium, tin, tantalum, zinc and tungsten. In particular, silicon and titanium are preferable from the viewpoint of availability.

($R^{32b}$)

$R^{32b}$ in the formula (C-2) corresponds to $R^{32b}$ in the formula (A-2). Accordingly, the detail of $R^{32b}$ is applied by the above description about $R^{3b}$.

($R^{42b}$)

$R^{42b}$ each independently represents an unsubstituted or a substituted hydrocarbon ligand, an unsubstituted or a substituted alkoxy ligands, amide ligands, and halide ligands different from —$OR^{32b}$.

Specific examples of the unsubstituted or the substituted hydrocarbon ligand, the unsubstituted or the substituted alkoxy ligands, amide ligands, and halide ligands different from —$OR^{32b}$ include ligands exemplified with respect to $R^{41b}$. When m2 is 2 to 5, a plurality of $R^{42b}$(s) may be the same as each other or different from each other, and all $R^{42b}$(s) are preferably the same as each other from the viewpoint of availability.

(n2')

n2' represents the oxidation number of M' and (n2'−m2') is an integer of 1 to 6.

(m2')

m2' represents an integer of 0 or more and (n2'-1) or less. In other words, it is an integer of 0 to 5.

Specific examples of the metal alkoxide represented by the formula (C-2) include metal alkoxides exemplified with respect to the formula (C-1). At least one selected from the group consisting of a titanium compound and a silicon compound is preferable, titanium tetramethoxide, titanium tetra-iso-propoxide, titanium tetra-n-butoxide, titanium tetra-t-butoxide, tetramethoxysilane, tetraethoxysilane, tetra-n-propoxysilane, and tetra-n-butoxysilane are more preferable, and titanium tetramethoxide, titanium tetra-isopropoxide, titanium tetra-n-butoxide, titanium tetra-t-butoxide, and tetramethoxysilane are further preferable, from the viewpoint of availability.

<B: 1-6. Reaction Step>

Examples of the reaction step include loading a carbamic acid salt and a metal alkoxide as raw materials into a sealed reaction vessel and reacting them at 200° C. for 48 hours. Alternatively, the reaction step includes placing an amine in a sealed reaction vessel, blowing a carbon dioxide-containing gas thereto to produce a carbamic acid salt, and then adding titanium alkoxide as the metal alkoxide thereto, and heating and reacting the resultant. Hereinafter, reaction conditions are described.

(Reaction Solvent)

The reaction step may be made with or without a reaction solvent, and is preferably made with a reaction solvent. The reaction solvent is not particularly limited in terms of the type thereof, and examples thereof preferably include ethers such as diethyl ether, tetrahydrofuran and 1,4-dioxane; nitriles such as acetonitrile and propionitrile; and aprotic polar solvents such as dimethylacetamide, N,N-dimethylformamide, N,N'-dimethylpropylene urea, 1,3-dimethyl-2-imidazolidinone and N-methylpyrrolidone. The reaction solvent is more preferably an aprotic solvent, further preferably an ether and an aprotic polar solvent, and is particularly preferably 1,4-dioxane which is an aprotic ether and N-methylpyrrolidone which is an aprotic solvent. The above-mentioned reaction solvent can be used to thereby more efficiently produce a carbamic acid ester. When the difference between the boiling point of the solvent and the boiling point of the product is large, purification can be easily made and the solvent can also be reused. The reaction solvent may be used singly or in combination of two or more thereof.

The amount of use of the reaction solvent is not particularly limited, and can be appropriately selected depending on an objective carbamic acid ester.

(Catalyst)

The reaction step in the present embodiment may also be performed in the presence of a catalyst. In particular, when alkoxysilane is used as the metal alkoxide, the reaction step is preferably performed in the presence of a catalyst. Examples of the catalyst preferably include an organic base carboxylic acid salt, an alkali metal salt, zinc compound, a titanium(IV) compound, and a zirconium(IV) compound.

Examples of the organic base carboxylic acid salt include an acetic acid salt of 1,8-diazabicyclo[5.4.0]undec-7-ene, an acetic acid salt of 1,5-diazabicyclo[4.3.0]non-5-ene, and a nitric acid salt of 1,1,3,3-tetramethylguanidine.

Examples of the alkali metal salt include alkali metal acetates such as lithium acetate, sodium acetate, potassium acetate, rubidium acetate and cesium acetate; alkali metal carbonates such as lithium carbonate, sodium carbonate, potassium carbonate, rubidium carbonate and cesium carbonate; alkali metal hydroxides such as lithium hydroxide, sodium hydroxide, potassium hydroxide, rubidium hydroxide and cesium hydroxide; and alkali metal alkoxides such as lithium alkoxide, sodium alkoxide, potassium alkoxide, rubidium alkoxide and cesium alkoxide.

Examples of the zinc compound include zinc halides such as zinc chloride and zinc bromide; zinc sulfate; zinc sulfonates such as zinc p-toluenesulfonate and zinc trifluoromethanesulfonate; and zinc carboxylate derivatives such as zinc formate, zinc acetate, zinc propionate, zinc octanoate, zinc salicylate, zinc pivalate, zinc acrylate, p-chlorobenzoic acid, zinc phenolate, zinc chloroacetate, zinc acetylacetonate, zinc oxalate and zinc trifluoroacetate, and a zinc (II)-1,10-phenanthroline complex.

Examples of the titanium(IV) compound include titanium (IV) oxysulfate-n-hydrate, $TiCl_4$, $TiBr_4$, $Ti(OC_2H_5)Cl_3$, $Ti(OC_5H_7)Cl_3$, and $Ti(O\text{-iso-}C_4H_9)Cl_3$.

Examples of the zirconium(IV) compound include zirconium(IV) chloride and zirconium(IV) oxychloride-octahydrate.

The catalyst may be produced from, for example, two or more compounds. For example, zinc acetate and 1,10-phenanthroline are charged into a reaction vessel to form a zinc(II)-1,10-phenanthroline (phen) complex and the complex may be used as the catalyst.

In particular, the zinc compound is preferably, for example, zinc acetate, zinc pivalate, a zinc(II)-1,10-phenanthroline (phen) complex, zinc p-toluenesulfonate or zinc trifluoromethanesulfonate, more preferably zinc acetate or a zinc(II)-1,10-phenanthroline (phen) complex.

The amount of use (amount of charging) of the catalyst in the reaction step is not particularly limited, is required to be appropriately selected depending on an objective carbamic acid ester, and is preferably 10 mol % or more, and 70 mol % or less, more preferably 50 mol % or less based on the molar number of the carbamic acid salt. Such catalysts may be used singly or in combination of two or more thereof.

(Reaction Temperature)

The temperature (sometimes designated as "reaction temperature".) in the reaction step is not particularly limited, and may be appropriately adjusted depending on the reaction scale and the like. It is usually 140° C. or more, preferably 150° C. or more, and usually 250° C. or less, preferably 210° C. or less.

(Reaction Time)

The reaction time is not particularly limited, and may be appropriately adjusted depending on the reaction temperature, the reaction scale, and the like. It is usually 30 minutes or more, preferably 1 hour or more, and usually 48 hours or less, preferably 24 hours or less, more preferably 20 hours or less.

(Reaction Atmosphere)

The atmosphere in the reaction step may be an air atmosphere, or may be an atmosphere of an inert gas such as nitrogen or argon. The reaction step may be under any of pressurizing and depressurizing conditions, and the pressure is usually 0.01 atm or more, preferably 0.05 atm or more, more preferably 0.1 atm or more, and usually 10 atm or less, preferably 5 atm or less, more preferably 2 atm or less.

(Reaction Vessel)

The reaction vessel is not particularly limited, and is required to be appropriately selected depending on a continuous process or a batch process. A continuous process or a batch process may be adopted in the present embodiment. In the case of a batch process, it is preferred to use a closed reaction vessel (sealed reaction vessel), and it is more preferred to use a closed reaction vessel which has the same volume as the volume of a mixture of the carbamic acid salt, the metal alkoxide, and, if necessary, the reaction solvent and the catalyst.

(Other Step(s))

The method for producing a carbamic acid ester according to the present embodiment may include any optional step other than the reaction step. Examples of such any optional step include the carbamic acid salt production step described in the section (Carbamic acid salt), a step of reproducing the metal alkoxide by an alcohol, and a purification step of increasing the purity of a carbamic acid ester. A purification method usually conducted in the organic synthesis field, such as filtration, adsorption, column chromatography, or distillation, can be adopted in the purification step.

Hereinafter, the third aspect of the present invention will be described.

<C: 1. Method for Producing Urea Derivative>

A method for producing a urea derivative according to one embodiment of the third aspect of the present invention includes a reaction step (hereinafter, sometimes abbreviated as "reaction step".) of heating a carbamic acid salt in the presence of a catalyst to produce a urea derivative having a structure represented by the following formula (b'), in which the catalyst is a metal-containing catalyst or an organic base catalyst.

(b')

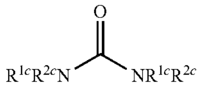

In the formula (b'), $R^{1c}$ each independently represents a hydrogen atom, or an unsubstituted or a substituted hydrocarbon group; and $R^{2c}$ each independently represents an unsubstituted or a substituted hydrocarbon group, provided that two $R^{2c}$(s) may be linked to each other to form a ring.

Specific examples of the reaction involving heating a carbamic acid salt to produce a urea derivative having a structure represented by the following formula (b') include the following reaction.

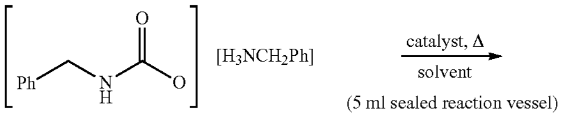

1

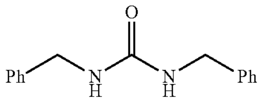

2

The reaction mechanism of the method for producing a urea derivative according to the present embodiment is considered, for example, as follows: when N-(2-ammonioethyl)carbamate is used as the carbamic acid salt as a reaction substrate and a metal-containing catalyst is used as the catalyst, N-(2-ammonioethyl)carbamate is coordinated by the metal-containing catalyst to increase electrophilicity of carbonyl carbon, nucleophilic attack of an amine moiety toward the carbonyl carbon occurs, dewatering occurs thereafter, and then ethylene urea is obtained (see the following reaction scheme).

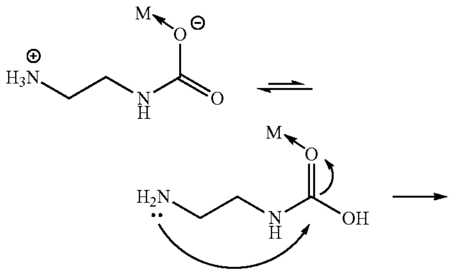

-continued

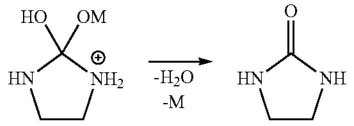

When N-(2-ammonioethyl)carbamate is used as the carbamic acid salt as a reaction substrate and an organic base catalyst is used as the catalyst, an ammonium moiety of N-(2-ammonioethyl)carbamate is deprotonated by the organic base catalyst to increase nucleophilicity, nucleophilic attack toward carbonyl carbon occurs, dewatering occurs thereafter, and then ethylene urea is obtained (see the following reaction scheme).

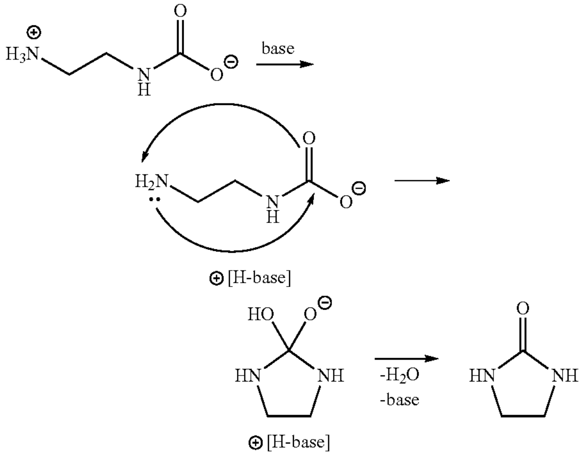

The production method according to the present embodiment can serve as an alternative method to a synthesis method using phosgene. As described below, a carbamic acid salt obtained by reacting an amino group-containing organic compound having one or more primary or secondary amino groups with carbon dioxide can be adopted as a raw material, thereby leading to effective utilization of carbon dioxide, and contributing to the reduction of greenhouse gas emissions. Specific examples of such a carbamic acid salt include a carbamic acid salt represented by formula (A'-1) or (A'-2).

In other words, in the present embodiment, the carbamic acid salt is preferably a carbamic acid salt represented by formula (A'-1) or (A'-2) and the urea derivative having the structure represented by the formula (b') is preferably a urea derivative represented by formula (B'-1) or (B'-2).

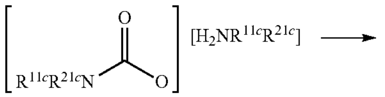

(A'-1)

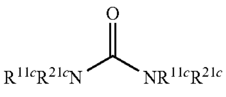

(B'-1)

In the formulae (A'-1) and (B'-1), $R^{11c}$ each independently represents a hydrogen atom, or an unsubstituted or a substituted hydrocarbon group; and $R^{21c}$ each independently represents an unsubstituted or a substituted hydrocarbon group.

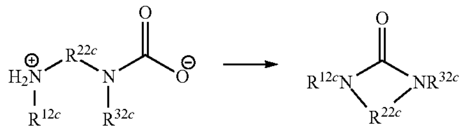

(A'-2) (B'-2)

In the formulae (A'-2) and (B'-2), $R^{12c}$ represents a hydrogen atom, or an unsubstituted or a substituted hydrocarbon group; $R^{22c}$ represents an unsubstituted or a substituted divalent hydrocarbon group; and $R^{32c}$ represents a hydrogen atom, or an unsubstituted or a substituted hydrocarbon group.

Hereinafter, the "urea derivative having the structure represented by the formula (b')", "carbamic acid salt", "catalyst", and the like are described in detail.

(Urea Derivative Having Structure Represented by Formula (b'))

A urea derivative having a structure represented by formula (b') is obtained by the production method according to the present embodiment.

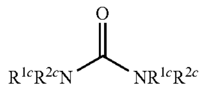

(b')

In the formula (b'), $R^{1c}$ each independently represents a hydrogen atom, or an unsubstituted or a substituted hydrocarbon group; and $R^{2c}$ each independently represents an unsubstituted or a substituted hydrocarbon group, provided that two $R^{2c}$(s) may be linked to each other to form a ring.

$(R_{1c})$ $R^{1c}$ each independently represents a hydrogen atom, or an unsubstituted or a substituted hydrocarbon group.

The "hydrocarbon group" in the description of the third aspect of the present invention is not herein limited to a linear saturated hydrocarbon group, and may have each of a carbon-carbon unsaturated bond, a branched structure, and a cyclic structure.

The number of carbon atoms in $R^{1c}$ is not particularly limited, and is usually 1 or more, and usually 30 or less, preferably 24 or less, more preferably 20 or less.

Examples of the unsubstituted hydrocarbon group represented by $R^{1c}$ include an alkyl group such as an ethyl group, a n-propyl group, an iso-propyl group, a n-butyl group, a sec-butyl group, an iso-butyl group, a tert-butyl group, a n-pentyl group, an iso-pentyl group, a neopentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-docosyl group; a cycloalkyl group such as a cyclopropyl group, a cyclobutyl group, a cyclopentyl group and a cyclohexyl group; and an aromatic hydrocarbon group such as a phenyl group, a 1-naphthyl group, a 2-naphthyl group, a 1-phenanthryl group, a 2-phenanthryl group, a 3-phenanthryl group, a 4-phenanthryl group, a 9-phenanthryl group, a 1-anthryl group, a 2-anthryl group, a 9-anthryl group, a 1-pyrenyl group, a 2-pyrenyl group, a 4-pyrenyl group, a 1-triphenylenyl group and a 2-triphenylenyl group.

When the hydrocarbon group represented by $R^{1c}$ has a substituent, examples of the substituent include a deuterium atom; an alkyl group having 1 to 4 carbon atoms, such as a methyl group, an ethyl group, a n-propyl group, an isopropyl group, a n-butyl group, a sec-butyl group, an isobutyl group and a tert-butyl group; a cycloalkyl group having 3 to 4 carbon atoms, such as a cyclopropyl group and a cyclobutyl group; an aromatic hydrocarbon group having 6 to 10 carbon atoms, such as a phenyl group, a 1-naphthyl group and a 2-naphthyl group; a heterocyclic group, for example, an oxygen-containing heterocyclic group such as a furanyl group, a sulfur-containing heterocyclic group such as a thienyl group, and a nitrogen-containing heterocyclic ring group, such as a pyrrolyl group and a pyridyl group; a hydroxyl group; and an alkoxy group. Accordingly, when the hydrocarbon group represented by $R^{1c}$ has a substituent, examples of $R^{1c}$ can preferably include an aralkyl group such as a benzyl group, a phenethyl group, a 1-naphthylmethyl group and a 2-naphthylmethyl group; a cycloalkylalkyl group such as a cyclohexylmethyl group; a hydrocarbon group each having an oxygen-containing heterocyclic ring, such as a furfuryl group; a hydrocarbon group each having a sulfur-containing heterocyclic ring, such as a thienylmethyl group; and a hydrocarbon group each having a nitrogen-containing heterocyclic ring, such as a pyridylmethyl group, and particularly preferably include a benzyl group.

When the hydrocarbon group has a substituent, the number of carbon atoms means the total number of carbon atoms of the number of carbon atoms in the substituent and the number of carbon atoms in the hydrocarbon group.

$R^{1c}$ is particularly preferably hydrogen from the viewpoint of usefulness of a urea derivative compound.

$(R^{2c})$ $R^{2c}$ each independently represents an unsubstituted or a substituted hydrocarbon group, provided that two $R^{2c}$(s) may be linked to each other to form a ring.

The number of carbon atoms in $R^{2c}$ is not particularly limited, and is usually 1 or more, and usually 30 or less, preferably 24 or less, more preferably 20 or less.

Examples of the unsubstituted hydrocarbon group represented by $R^{2c}$ include an alkyl group such as an ethyl group, a n-propyl group, an iso-propyl group, a n-butyl group, a sec-butyl group, an iso-butyl group, a tert-butyl group, a n-pentyl group, an iso-pentyl group, a neopentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-docosyl group; a cycloalkyl group such as a cyclopropyl group, a cyclobutyl group, a cyclopentyl group and a cyclohexyl group; and an aromatic hydrocarbon group such as a phenyl group, a 1-naphthyl group, a 2-naphthyl group, a 1-phenanthryl group, a 2-phenanthryl group, a 3-phenanthryl group, a 4-phenanthryl group, a 9-phenanthryl group, a 1-anthryl group, a 2-anthryl group, a 9-anthryl group, a 1-pyrenyl group, a 2-pyrenyl group, a 4-pyrenyl group, a 1-triphenylenyl group and a 2-triphenylenyl group.

When the hydrocarbon group represented by $R^{2c}$ has a substituent, examples of the substituent include a deuterium atom; an alkyl group having 1 to 4 carbon atoms, such as a methyl group, an ethyl group, a n-propyl group, an isopropyl group, a n-butyl group, a sec-butyl group, an isobutyl group and a tert-butyl group; a cycloalkyl group having 3 to 4 carbon atoms, such as a cyclopropyl group and a cyclobutyl group; an aromatic hydrocarbon group having 6 to 10 carbon atoms, such as a phenyl group, a 1-naphthyl group and a 2-naphthyl group; a heterocyclic group, for example, an oxygen-containing heterocyclic group such as a furanyl group, a sulfur-containing heterocyclic group such as a thienyl group, and a nitrogen-containing heterocyclic ring group, such as a pyrrolyl group and a pyridyl group. Accordingly, when the hydrocarbon group represented by $R^{2c}$ has a substituent, examples of $R^{2c}$ can preferably include an aralkyl group such as a benzyl group, a phenethyl group, a 1-naphthylmethyl group and a 2-naphthylmethyl group; a cycloalkylalkyl group such as a cyclohexylmethyl group; a hydrocarbon group each having an oxygen-containing heterocyclic ring, such as a furfuryl group; a hydrocarbon group each having a sulfur-containing heterocyclic ring, such as a thienylmethyl group; and a hydrocarbon group each having a nitrogen-containing heterocyclic ring, such as a pyridylmethyl group, and particularly preferably include a benzyl group.

When the hydrocarbon group has a substituent, the number of carbon atoms means the total number of carbon atoms of the number of carbon atoms in the substituent and the number of carbon atoms in the hydrocarbon group. Two $R^{2c}$(s) may be linked to form a ring, provided that the number of carbon atoms in the ring is 20 or less. The number of carbon atoms in the ring is preferably 2 or more, and preferably 10 or less, more preferably 7 or less.

$R^{2c}$ is particularly preferably a benzyl group from the viewpoint of availability of raw materials. When $R^{2c}$(s) are linked to form a ring, an ethylene group is preferable from the viewpoint of usefulness of a urea derivative compound.

The urea derivative having the structure represented by the formula (b') is preferably a compound represented by formula (B'-1) or a compound represented by formula (B'-2).

(B'-1)

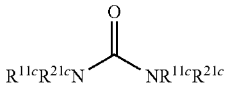

(B'-2)

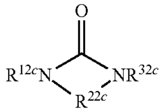

In the formula (B'-1), $R^{11c}$ each independently represents a hydrogen atom, or an unsubstituted or a substituted hydrocarbon group, and $R^{21c}$ each independently represents an unsubstituted or a substituted hydrocarbon group.

In the formula (B'-2), $R^{12c}$ represents a hydrogen atom, or an unsubstituted or a substituted hydrocarbon group, $R^{22c}$ represents an unsubstituted or a substituted divalent hydrocarbon group, and $R^{32c}$ represents a hydrogen atom, or an unsubstituted or a substituted hydrocarbon group.

($R^{11c}$, $R^{12c}$, $R^{32c}$)

$R^{11c}$, $R^{12c}$, and $R^{32c}$ each independently represents a hydrogen atom, or an unsubstituted or a substituted hydrocarbon group.

The details of $R^{11c}$, $R^{12c}$, and $R^{32c}$ are applied by the above description about $R^{1c}$.

($R^{21c}$)

$R^{21c}$ each independently represents an unsubstituted or a substituted hydrocarbon group.

The detail of $R^{21c}$ is applied by the above description about $R^{2c}$.

($R^{22c}$)

$R^{22c}$ represents an unsubstituted or a substituted divalent hydrocarbon group.

Examples of the divalent hydrocarbon group include a methylene group; an ethylene group; a linear, branched or cyclic alkylene group having 3 or more carbon atoms; or an arylene group having 6 or more carbon atoms.

The number of carbon atoms in the divalent hydrocarbon group is not particularly limited, and is preferably 2 or more, and preferably 20 or less, more preferably 10 or less. The divalent hydrocarbon group may have an unsaturated bond. When the divalent hydrocarbon group has a substituent, the number of carbon atoms in the divalent hydrocarbon group means the number of carbon atoms also including the number of carbon atoms in the substituent. Examples of the substituent include those exemplified in the description in the section ($R^{1c}$).

Specific examples of $R^{22c}$ include a linear hydrocarbon group such as a methylene group, an ethylene group, a tetramethylethylene group, a n-propylene group (trimethylene group), a 1-methylpropylene group, a 1,1-dimethylpropylene group, a 2-methylpropylene group, a 1,2-dimethylpropylene group, a 2,2-dimethylpropylene group, a 1,1,2-trimethylpropylene group, a 1,1,3-trimethylpropylene group, a n-butylene group (tetramethylene group), a 2-methyl-1,4-butylene group, a 3-methyl-1,4-butylene group, a 2,2-dimethyl-1,4-butylene group, a 2,3-dimethyl-1,4-butylene group, a 2,2,3-trimethyl-1,4-butylene group, a n-pentylene group (pentamethylene group) and a n-hexanylene group (hexamethylene group); an alicyclic hydrocarbon group such as a 1,4-cyclohexylene group; a 1,4-phenylene group, a 1,2-phenylene group and a 1,3-phenylene group, each obtained by removal of two hydrogen atoms from a benzene ring; an aromatic hydrocarbon group such as a dimethylphenylene group (xylyl group) obtained by removal of two hydrogen atoms from a benzene ring of xylene, a methylphenylene group (tolylene group) obtained by removal of two hydrogen atoms from a benzene ring of toluene, and a naphthanylene group obtained by removal of two hydrogen atoms from naphthalene; and a divalent group including an aliphatic hydrocarbon group and an aromatic hydrocarbon group, such as a 1,4-phenylenebis(methylene) group, a 1,4-phenylenebis(ethylene) group, a group obtained by removal of one hydrogen atom from each of two benzene rings of biphenyl, and a group obtained by removal of one hydrogen atom from each of two benzene rings of diphenylmethane.

Specific examples of the compound represented by the formula (B'-1) include N,N'-diethylurea, N,N'-di-n-propylurea, N,N'-di-n-butylurea, N,N'-di-t-butylurea, N,N'-di-n-pentylurea, N,N'-di-n-hexylurea, N,N'-di-n-octylurea, N,N'-di-i-propylurea, N,N'-bis-(2-ethylhexyl)urea, N,N'-dicyclohexylurea, N,N'-bis-(2-hydroxyethyl)urea, N,N'-bis-(3-hydroxy-n-propyl)urea, N,N'-bis-(2-hydroxy-n-propyl) urea, N,N'-bis-(2,3-dihydroxy-n-propyl)urea, N,N'-bis-(2-methoxyethyl)urea, N,N'-bis-(2-ethoxyethyl)urea, N,N'-bis-(2-aminoethyl)urea, N,N'-diphenylurea, N,N'-dibenzylurea, and N,N'-bis-(2-phenylethyl)urea. The production method of the present embodiment is particularly suitable for production of N,N'-di-t-butylurea, N,N'-dicyclohexylurea, or N,N'-dibenzylurea.

Specific examples of the compound represented by the formula (B'-2) include ethylene urea, N,N'-dimethylpropylene urea, and 1,3-dimethyl-2-imidazolidinone. The production method of the present embodiment is particularly suitable for production of ethylene urea.

(Carbamic Acid Salt)

A specific type of the carbamic acid salt in the reaction step is not particularly limited and is required to be appropriately selected depending on an objective urea derivative, and preferable examples include a carbamic acid salt represented by formula (A'-1) and a carbamic acid salt represented by formula (A'-2).

(A'-1)

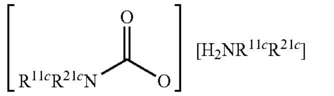

(A'-2)

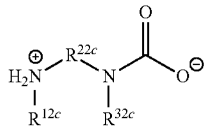

In the formula (A'-1), $R^{11c}$ each independently represents a hydrogen atom, or an unsubstituted or a substituted hydrocarbon group; and $R^{21c}$ each independently represents an unsubstituted or a substituted hydrocarbon group.

In the formula (A'-2), $R^{12c}$ represents a hydrogen atom, or an unsubstituted or a substituted hydrocarbon group; $R^{22c}$ represents an unsubstituted or a substituted hydrocarbon group; and $R^{32c}$ represents a hydrogen atom, or an unsubstituted or a substituted hydrocarbon group.

The details of $R^{11c}$, $R^{12c}$, and $R^{32c}$ are applied by the above description about $R^{11c}$, $R^{12c}$, and $R^{32c}$ in the section "Urea derivative having structure represented by formula (b')".

The detail of $R^{21c}$ is applied by the above description about $R^{21c}$ in the section "Urea derivative having structure represented by formula (b')".

The detail of $R^{22c}$ is applied by the above description about $R^{22c}$ in the section "Urea derivative having structure represented by formula (b')".

The method for producing the carbamic acid salt is not particularly limited, and the carbamic acid salt can be produced by, for example, the method for producing a carbamic acid salt according to the first aspect of the present invention. Alternatively, one can be used which is produced by a reaction of an amino group-containing organic compound having one or more primary or secondary amino groups, more specifically an aliphatic monoamine such as benzylamine or hexylamine, or an aliphatic diamine such as ethylenediamine, with carbon dioxide. The carbon dioxide for use in the reaction can be a pure carbon dioxide gas, or can also be a mixed gas containing carbon dioxide at a partial pressure of at 1 atm or less, for example, a mixed gas having a content rate of carbon dioxide of 0.01% or more in terms of volume ratio.

In the present embodiment, it is preferable to further include a carbamic acid salt production step of contacting an amino group-containing organic compound with a carbon dioxide-containing mixed gas in a solvent to produce the carbamic acid salt. The volume of carbon dioxide in the carbon dioxide-containing mixed gas is usually 0.01% or more, preferably 1% or more, more preferably 15% or more, and preferably 50% or less. The solvent for use in the carbamic acid salt production step is not particularly limited, and a hydrocarbon-based solvent such as hexane, benzene, or toluene can be preferably used. The reaction time may be appropriately adjusted depending on the partial pressure of carbon dioxide in the carbon dioxide-containing mixed gas, and the reaction scale. For example, when the volume of carbon dioxide in the carbon dioxide-containing mixed gas is 15%, 1 mmol of the amino group-containing organic compound as a raw material can be reacted for 5 minutes or more and 10 minutes or less to synthesize a carbamic acid salt at a yield of 80% or more. When 40 mmol of the amino group-containing organic compound is used, a yield of 90% or more can be achieved by a reaction time of about 180 minutes. Such a carbamic acid salt generated can be easily isolated by filtration.

It has been confirmed that the carbamic acid salt production step, specifically, for example, a reaction shown by the following scheme can produce a carbamic acid salt at a high yield of, for example, 99% or more. It has been found that synthesis using a mixed gas of low partial pressure carbon dioxide as shown in Examples described below also provides a carbamic acid salt at a high yield of isolation of 93%.

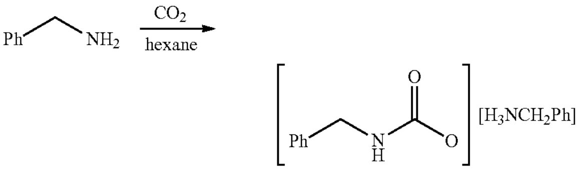

While a method for producing a urea derivative with an amine and carbon dioxide as raw materials has been heretofore reported, such a production method has used carbon dioxide at a high pressure (for example, C. Wu, H. Cheng, R. Liu, Q. Wang, Y. Hao, Y. Yu, F. Zhao, Green Chem. 2010, 12, 1811-1816.). There has also been proposed a method for producing a urea derivative by use of carbon dioxide at ordinary pressure (for example, M. J. Fuchter, C. J. Smith, M. W. S. Tsang, A. Boyer, S. Saubem, J. H. Ryan, A. B. Holmes, Chem. Commun. 2008, 2152-2154., M. T. Zoeckler, R. M. Lame, J. Org. Chem. 1983, 48, 2539-2543., M. Xu, Andrew R. Jupp, D. W. Stephan, Angew. Chem. Int. Ed. 2017, 56, 14277-14281.).

In this regard, the production method of the present embodiment can also use a mixed gas where carbon dioxide is at a low partial pressure. An exhaust gas in a thermal power plant usually includes about 15% of carbon dioxide, and a method involving producing a carbamic acid salt with such a low-concentration carbon dioxide-containing mixed gas and then producing a urea derivative therefrom is also effective for the reduction of greenhouse gas emissions.

(Catalyst)

The catalyst used in the reaction step is a metal-containing catalyst or an organic base catalyst.

Examples of the metal-containing catalyst preferably include a titanium-based catalyst, a tin-based catalyst, a zirconium-based catalyst, a hafnium-based catalyst, a palladium-based catalyst, an aluminum-based catalyst, an alkali metal-based catalyst, and a zinc-based catalyst, more preferably include a titanium-based catalyst, a tin-based catalyst, a hafnium-based catalyst, and an alkali metal-based catalyst. Examples of the tin-based catalyst preferably include organic tin compounds such as dibutyltin oxide ($Bu_2SnO$), dibutyltin diacetate ($Bu_2Sn(OAc)_2$), dibutyltin dilaurate ($Bu_2Sn(OOC(CH_2)_{10}CH_3)_2$), and dibutyltin dimethoxide ($Bu_2Sn(OMe)_2$). Examples of the titanium-based catalyst preferably include titanium complexes such as $Ti(OMe)_4$, $Ti(Cp)_2Cl_2$, and $Ti(Cp)_2(OTf)_2$. Examples of the zirconium-based catalyst include zirconium complexes such as $Zr(Cp)_2Cl_2$ and $Ti(Cp)_2(OTf)_2$. Examples of the hafnium-based catalyst preferably include organic hafnium compounds such as hafnium(IV) ethoxide, hafnium(IV) isopropoxide, and hafnium(IV) trifluoromethanesulfonate ($Hf(OTf)_4$); and hafnium complexes such as hafnium(IV) acetylacetonate and hafnocene dichloride. Examples of the palladium-based catalyst include palladium complexes such as tetrakis(acetonitrile)palladium(II) bis(tetrafluoroborate) ($[Pd(MeCN)_4](BF_4)_2$) and tetrakis(benzonitrile)palladium (II) bis(tetrafluoroborate) ($[Pd(PhCN)_4](BF_4)_2$). Examples of the aluminum-based catalyst include $AlCl_3$ and $Al(OTf)_3$. Examples of the alkali metal-based catalyst include alkali metal carbonates such as sodium carbonate, potassium carbonate ($K_2CO_3$), and cesium carbonate. Examples of the zinc-based catalyst include organic zinc compounds such as zinc acetate; and zinc complexes such as a zinc(II)-1,10-phenanthroline complex. The metal-containing catalyst may be produced from, for example, two or more compounds. For example, zinc acetate and 1,10-phenanthroline are charged into a reaction vessel to form a zinc(II)-1,10-phenanthroline (phen) complex and the complex may be used as the catalyst. Examples particularly preferably include $Bu_2SnO$, $Ti(OMe)_4$, $Ti(Cp)_2Cl_2$, $Ti(Cp)_2(OTf)_2$, $Hf(OTf)_4$, and $K_2CO_3$, among such metal-containing catalysts.

Examples of the organic base catalyst preferably include an amine-based catalyst and a phosphine-based catalyst, more preferably include an amine-based catalyst. Examples of the amine-based catalyst include 1,1,3,3-tetramethylguanidine, 1,8-diazabicyclo[5.4.0]-7-undecene, 7-methyl-1,5,7-triazabicyclo[4.4.0]dec-5-ene, 1,5-diazabicyclo[4.3.0]non-5-ene, 1,5,7-triazabicyclo[4.4.0]dec-5-ene, 4-dimethylaminopyridine, and 1,8-bis(dimethylamino) naphthalene. Examples of the phosphine-based catalyst include t-butylimino-tris(dimethylamino)phosphorane, phosphazene base P1-tBu-tris(tetramethylene), phosphazene base P2-Et(P2-Et), and 2,8,9-triisobutyl-2,5,8,9-tetraaza-1-phosphabicyclo[3.3.3]undecane.

The amount of use (amount of charging) of the catalyst in the reaction step is not particularly limited, is required to be appropriately selected depending on an objective urea derivative, and is preferably 10 mol % or more, and 70 mol % or less, more preferably 50 mol % or less based on the molar number of the carbamic acid salt. Such catalysts may be used singly or in combination of two or more thereof.

(Reaction Solvent)

The reaction step may be made with or without a reaction solvent, and is preferably made with a reaction solvent. The reaction solvent is not particularly limited in terms of the type thereof, and examples thereof preferably include ethers such as diethyl ether and tetrahydrofuran; nitriles such as acetonitrile and propionitrile; and aprotic polar solvents such as dimethylacetamide, N,N-dimethylformamide, N,N'-dimethylpropylene urea, 1,3-dimethyl-2-imidazolidinone and N-methylpyrrolidone. In particular, such an aprotic polar solvent is more preferable, and 1,3-dimethyl-2-imidazolidinone or N-methyl-2-pyrrolidone is further preferable. The above-mentioned reaction solvents can be used to thereby more efficiently produce a urea derivative. When the difference between the boiling point of the solvent and the boiling point of the product is large, purification can be easily made and the solvent can also be reused. The reaction solvent may be used singly or in combination of two or more thereof.

The amount of use of the reaction solvent is not particularly limited, and can be appropriately selected depending on an objective urea derivative.

(Reaction Temperature)

In the present embodiment, a urea derivative is produced by heating the carbamic acid salt. The temperature (sometimes designated as "reaction temperature".) in the reaction step is usually 140° C. or more, preferably 160° C. or more, more preferably 180° C. or more, and usually 250° C. or less, preferably 200° C. or less.

(Reaction Time)

The reaction time is not particularly limited, and may be appropriately adjusted depending on the reaction temperature, the reaction scale, and the like. It is usually 30 minutes or more, preferably 1 hour or more, and usually 48 hours or less, preferably 24 hours or less, more preferably 20 hours or less.

(Reaction Atmosphere)

The atmosphere in the reaction step may be an air atmosphere, or may be an atmosphere of an inert gas such as nitrogen or argon. The reaction step may be under any of pressurizing and depressurizing conditions, and the pressure is usually 0.01 atm or more, preferably 0.05 atm or more, more preferably 0.1 atm or more, and usually 10 atm or less, preferably 5 atm or less, more preferably 2 atm or less.

(Reaction Vessel)

The reaction vessel is not particularly limited, and is required to be appropriately selected depending on a continuous process or a batch process. A continuous process or a batch process may be adopted in the present embodiment. In the case of a batch process, it is preferred to use a closed reaction vessel (sealed reaction vessel), and it is more preferred to use a closed reaction vessel which has the same volume as the volume of a mixture of the carbamic acid salt, the catalyst, and the reaction solvent.

(Other Step(s))

The method for producing a urea derivative according to the present embodiment may include any optional step other than the reaction step. Examples of such any optional step include the carbamic acid salt production step described in the section (Carbamic acid salt) and a purification step of increasing the purity of a urea derivative. A purification method usually conducted in the organic synthesis field, such as filtration, adsorption, column chromatography, or distillation, can be adopted in the purification step.

EXAMPLES

While the present invention is further specifically described below with reference to Examples, the present invention can be appropriately modified without departing from the gist thereof. Accordingly, the scope of the present invention should not be interrupted to be limited by specific examples shown below. Each compound was confirmed by various spectrophotometric analyses, unless particularly noted. Specifically, such each compound was analyzed by proton and $^{13}C$ nuclear magnetic resonance spectra ($^1H$-NMR, $^{13}C$-NMR). Mesitylene was used as the internal standard in calculation of the yield by such nuclear magnetic resonance spectra.

Examples of the First Aspect of the Present Invention

Example 1

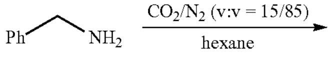

-continued

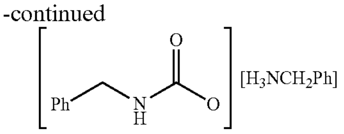

Benzylamine (40 g, 373 mmol) and hexane (1 L) were added into a reaction vessel, and a carbon dioxide/nitrogen mixed gas (1 atm, v:v=15:85) was allowed to pass at a flow rate of 0.5 L/min for 3 hours. After completion of the reaction, a white precipitate generated was separated by filtration, washed with hexane and thereafter dried in vacuum, and thus benzylammonium N-benzylcarbamate was obtained at a yield of 93%.

Example 2

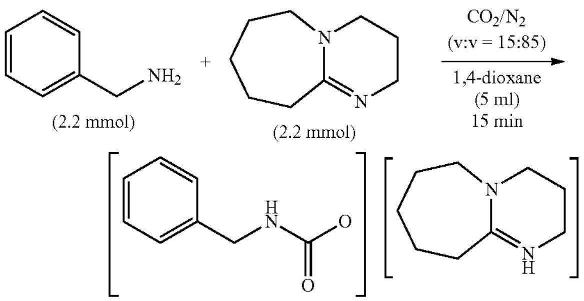

Benzylamine (229 mg, 2.2 mmol), 1,8-diazabicyclo[5.4.0]undec-7-ene (338 mg, 2.2 mmol), and 1,4-dioxane (5 mL) were added into a reaction vessel, and a carbon dioxide/nitrogen mixed gas (1 atm, v:v=15:85) was allowed to pass at a flow rate of 0.3 L/min for 15 minutes. After completion of the reaction, a solution was partially subjected to $^1H$ NMR measurement, and it was confirmed that a carbamic acid salt was quantitatively produced.

Example 3

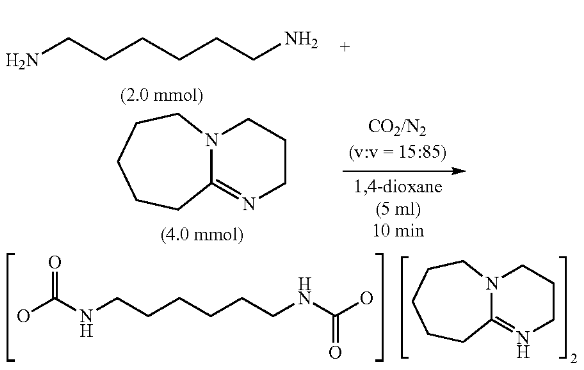

Hexamethylenediamine (232 mg, 2.0 mmol), 1,8-diazabicyclo[5.4.0]undec-7-ene (609 mg, 4.0 mmol), and 1,4-dioxane (5 mL) were added into a reaction vessel, and a carbon dioxide/nitrogen mixed gas (1 atm, v:v=15:85) was allowed to pass at a flow rate of 0.3 L/min for 10 minutes. After completion of the reaction, a solution and a semi-solid precipitated were partially subjected to $^1H$ NMR measurement, and it was confirmed that a carbamic acid salt was quantitatively produced.

Example 4

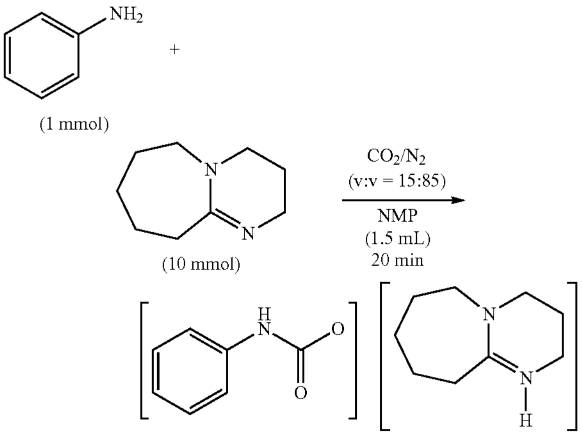

Aniline (186 mg, 2.0 mmol), 1,8-diazabicyclo[5.4.0]undec-7-ene (1.52 g, 10.0 mmol), and N-methylpyrrolidone (1.5 mL) were added into a reaction vessel, and a carbon dioxide/nitrogen mixed gas (1 atm, v:v=15:85) was allowed to pass at a flow rate of 0.1 L/min for 20 minutes. After completion of the reaction, a solution was partially subjected to $^1H$ NMR measurement, and it was confirmed that a carbamic acid salt was quantitatively produced.

Example 5

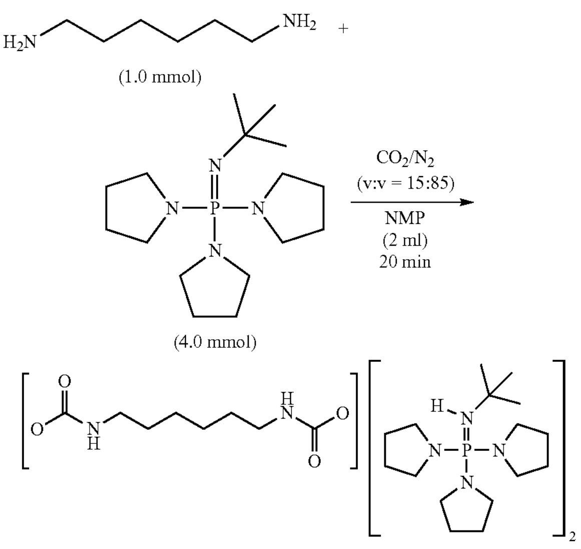

Hexamethylenediamine (116 mg, 1.0 mmol), tert-butylimino-tri(pyrrolidino)phosphorane (1250 mg, 4.0 mmol), and N-methylpyrrolidone (2 mL) were added into a reaction vessel, and a carbon dioxide/nitrogen mixed gas (1 atm, v:v=15:85) was allowed to pass at a flow rate of 0.3 L/min for 20 minutes. After completion of the reaction, a solution was partially subjected to $^{1}H$ NMR measurement, and it was confirmed that a carbamic acid salt was quantitatively produced.

Examples of the Second Aspect of the Present Invention

Example 1-1

Benzylammonium N-benzylcarbamate (2.0 mmol), titanium tetramethoxide (2.0 mmol), and 1,4-dioxane (5 mL) were added into a sealed reaction vessel having a volume of 5 mL, and reacted at 200° C. for 48 hours. The yield of an N-benzylcarbamic acid alkyl ester was 8%. The yield was determined with mesitylene (50 mg) as an internal standard according to $^{1}H$ NMR.

Example 1-2

An N-benzylcarbamic acid alkyl ester was obtained in the same manner as in Example 1-1 except that the reaction temperature was changed as shown in Table 1. The yield is shown in Table 1.

Example 1-3

An N-benzylcarbamic acid alkyl ester was obtained in the same manner as in Example 1-2 except that the reaction time was changed as shown in Table 1. The yield is shown in Table 1.

Example 1-4

An N-benzylcarbamic acid alkyl ester was obtained in the same manner as in Example 1-1 except that the metal alkoxide and the amount of the solvent were changed as shown in Table 1. The yield is shown in Table 1.

Example 1-5

An N-benzylcarbamic acid alkyl ester was obtained in the same manner as in Example 1-4 except that the reaction temperature was changed as shown in Table 1. The yield is shown in Table 1.

Example 1-6

An N-benzylcarbamic acid alkyl ester was obtained in the same manner as in Example 1-5 except that the reaction temperature was changed as shown in Table 1. The yield is shown in Table 1.

Example 1-7

An N-benzylcarbamic acid alkyl ester was obtained in the same manner as in Example 1-1 except that the metal alkoxide and the amount of the solvent were changed as shown in Table 1. The yield is shown in Table 1.

Example 1-8

An N-benzylcarbamic acid alkyl ester was obtained in the same manner as in Example 1-7 except that the reaction temperature was changed as shown in Table 1. The yield is shown in Table 1.

Example 1-9

An N-benzylcarbamic acid alkyl ester was obtained in the same manner as in Example 1-7 except that the reaction time and the reaction temperature were changed as shown in Table 1. The yield is shown in Table 1.

Example 1-10

An N-benzylcarbamic acid alkyl ester was obtained in the same manner as in Example 1-7 except that the reaction temperature was changed as shown in Table 1. The yield is shown in Table 1.

Example 1-11

An N-benzylcarbamic acid alkyl ester was obtained in the same manner as in Example 1-1 except that the metal alkoxide and the amount of the solvent were changed as shown in Table 1. The yield is shown in Table 1.

Example 1-12

An N-benzylcarbamic acid alkyl ester was obtained in the same manner as in Example 1-11 except that the reaction temperature was changed as shown in Table 1. The yield is shown in Table 1.

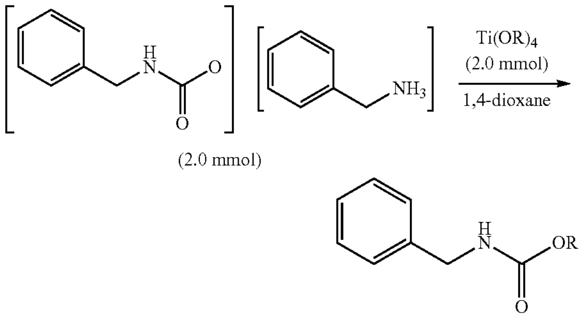

TABLE 1

| Example No. | Metal Alkoxide | Amount of Solvent (mL) | Reaction Time (h) | Reaction Temperature (° C.) | NMR Yield (%) |
|---|---|---|---|---|---|
| 1-1 | $Ti(OMe)_4$ | 5.0 | 1 | 200 | 8 |
| 1-2 | $Ti(OMe)_4$ | 5.0 | 1 | 170 | 3 |
| 1-3 | $Ti(OMe)_4$ | 5.0 | 15 | 170 | 13 |
| 1-4 | $Ti(O^{i}Pr)_4$ | 4.5 | 1 | 200 | 21 |
| 1-5 | $Ti(O^{i}Pr)_4$ | 4.5 | 1 | 170 | 12 |
| 1-6 | $Ti(O^{i}Pr)_4$ | 4.5 | 1 | 150 | 4 |
| 1-7 | $Ti(O^{n}Bu)_4$ | 4.0 | 1 | 200 | 30 |
| 1-8 | $Ti(O^{n}Bu)_4$ | 4.0 | 1 | 170 | 22 |
| 1-9 | $Ti(O^{n}Bu)_4$ | 4.0 | 48 | 170 | 43 |
| 1-10 | $Ti(O^{n}Bu)_4$ | 4.0 | 1 | 150 | 5 |
| 1-11 | $Ti(O^{t}Bu)_4$ | 4.0 | 1 | 200 | 3 |
| 1-12 | $Ti(O^{t}Bu)_4$ | 4.0 | 1 | 170 | 4 |

It has been indicated from Examples 1-1 to 1-12 that a carbamic acid alkyl ester can be produced by use of various titanium compounds as a metal alkoxide.

Example 2-1

Benzylammonium N-benzylcarbamate (2.0 mmol), tetramethoxysilane (2.0 mmol), zinc acetate (0.2 mmol), and 1,4-dioxane (4.5 mL) were added into a sealed reaction vessel having a volume of 5 mL, and reacted at 200° C. for 1 hour. The yield of N-benzylcarbamic acid methyl ester was 18%. The yield was determined with mesitylene (50 mg) as an internal standard according to $^{1}$H NMR.

Example 2-2

An N-benzylcarbamic acid alkyl ester was obtained in the same manner as in Example 2-1 except that the reaction temperature was changed as shown in Table 2. The yield is shown in Table 2.

Example 2-3

An N-benzylcarbamic acid alkyl ester was obtained in the same manner as in Example 2-2 except that the reaction time was changed as shown in Table 2. The yield is shown in Table 2.

Example 2-4

An N-benzylcarbamic acid alkyl ester was obtained in the same manner as in Example 2-3 except that the reaction temperature was changed as shown in Table 2. The yield is shown in Table 2.

Example 2-5

An N-benzylcarbamic acid alkyl ester was obtained in the same manner as in Example 2-3 except that the catalyst was changed as shown in Table 2. The yield is shown in Table 2. In Table 2, phen represents 1,10-phenanthroline.

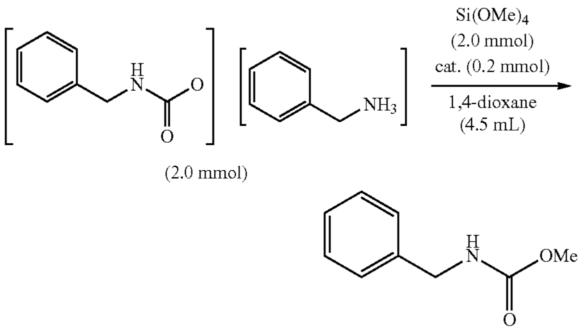

TABLE 2

| Example No. | cat. | Reaction Time (h) | Reaction Temperature (° C.) | NMR Yield (%) |
|---|---|---|---|---|
| 2-1 | $Zn(OAc)_2$ | 1 | 200 | 18 |
| 2-2 | $Zn(OAc)_2$ | 1 | 170 | 4 |
| 2-3 | $Zn(OAc)_2$ | 15 | 170 | 31 |
| 2-4 | $Zn(OAc)_2$ | 15 | 150 | 7 |
| 2-5 | $Zn(OAc)_2$ + phen (0.6 mmol) | 15 | 170 | 34 |

It has been indicated that a carbamic acid alkyl ester can be produced by use of a silicon compound as a metal alkoxide.

Example 3-1

Benzylamine (2.0 mmol), 1,8-diazabicyclo[5.4.0]undec-7-ene (2.0 mmol), and 1,4-dioxane (4.5 mL) were added into a sealed reaction vessel having a volume of 5 mL, and a $CO_2/N_2$ mixed gas (1 atm, v:v=15:85) was allowed to pass for 15 minutes. Subsequently, titanium tetramethoxide (2.0 mmol) was added thereto, and the resulting mixture was reacted at 200° C. for 1 hour. The yield of N-benzylcarbamic acid methyl ester was 50%. The yield was determined with mesitylene (50 mg) as an internal standard according to $^{1}$H NMR.

Example 3-2

An N-benzylcarbamic acid alkyl ester was obtained in the same manner as in Example 3-1 except that the reaction temperature was changed as shown in Table 3. The yield is shown in Table 3.

Example 3-3

An N-benzylcarbamic acid alkyl ester was obtained in the same manner as in Example 3-1 except that the volume ratio of the $CO_2/N_2$ mixed gas was changed as shown in Table 3. The yield is shown in Table 3.

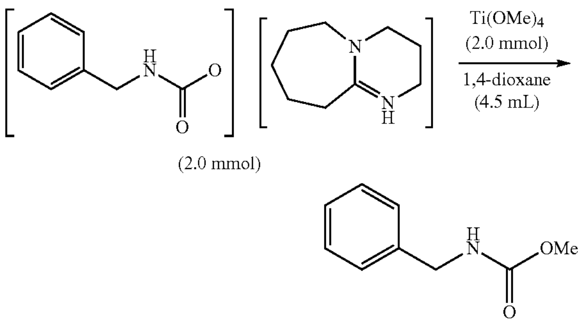

TABLE 3

| Example No. | Volume Ratio of $CO_2/N_2$ mixed gas | Reaction Time (h) | Reaction Temperature (° C.) | NMRYield (%) |
|---|---|---|---|---|
| 3-1 | 15/85 | 1 | 200 | 50 |
| 3-2 | 15/85 | 1 | 170 | 36 |
| 3-3 | 100/0 | 1 | 200 | 61 |

Example 4-1

A mixed solution including a dicarbamic acid salt prepared by allowing a carbon dioxide/nitrogen mixed gas (1 atm, v:v=15:85) to pass a mixture of hexamethylenediamine (116 mg, 1.0 mmol), 1,8-diazabicyclo[5.4.0]undec-7-ene (457 g, 3.0 mmol), and N-methylpyrrolidone (1.0 mL), at a flow rate of 0.1 L/min for 20 minutes, was added into a sealed reaction vessel having a volume of 5 mL, titanium tetrabutoxide (680 mg, 2.0 mmol) and N-methylpyrrolidone (3.6 mL) were added thereto, and the resulting mixture was reacted at 180° C. for 3 hours. The yield of N,N'-hexamethylenebis(dibutylcarbamate) was 60%. The yield was determined with mesitylene (50 mg) as an internal standard according to $^{1}$H NMR.

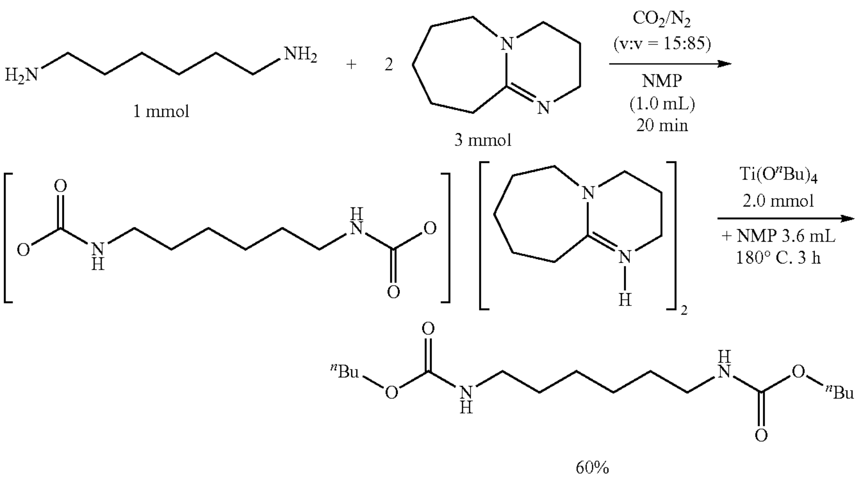

Example 4-2

A mixed solution including a carbamic acid salt prepared by allowing a carbon dioxide/nitrogen mixed gas (1 atm, v:v=15:85) to pass a mixture of aniline (186 mg, 2.0 mmol), 1,8-diazabicyclo[5.4.0]undec-7-ene (1.52 g, 10.0 mmol), and N-methylpyrrolidone (1.5 mL), at a flow rate of 0.1 L/min for 20 minutes, was added into a sealed reaction vessel having a volume of 5 mL, titanium tetrabutoxide (680 mg, 2.0 mmol) and N-methylpyrrolidone (1.6 mL) were added thereto, and the resulting mixture was reacted at 180° C. for 3 hours. The yield of butyl-N-phenylcarbamate was 40%. The yield was determined with mesitylene (50 mg) as an internal standard according to $^{1}H$ NMR.

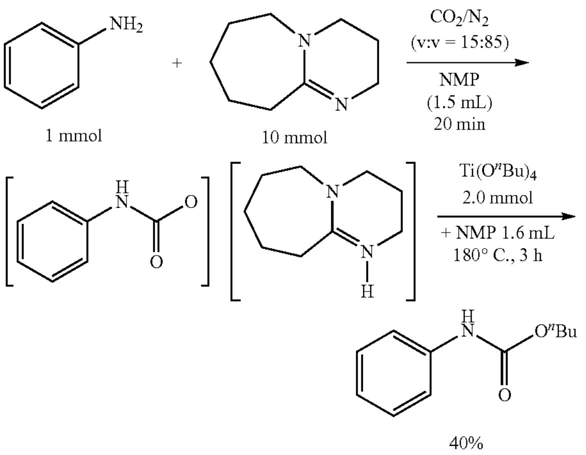

Example 4-3

A mixed solution including a dicarbamic acid salt prepared by allowing a carbon dioxide/nitrogen mixed gas (1 atm, v:v=15:85) to pass a mixture of hexamethylenediamine (116 mg, 1.0 mmol), tert-butylimino-tri(pyrrolidino)phosphorane (1250 mg, 4.0 mmol), and N-methylpyrrolidone (2.0 mL), at a flow rate of 0.1 L/min for 20 minutes, was added into a sealed reaction vessel having a volume of 5 mL, titanium tetrabutoxide (680 mg, 2.0 mmol) and N-methylpyrrolidone (3.6 mL) were added thereto, and the resulting mixture was reacted at 180° C. for 3 hours. The yield of N,N'-hexamethylenebis(dibutylcarbamate) was 52%. The yield was determined with mesitylene (50 mg) as an internal standard according to $^{1}H$ NMR.

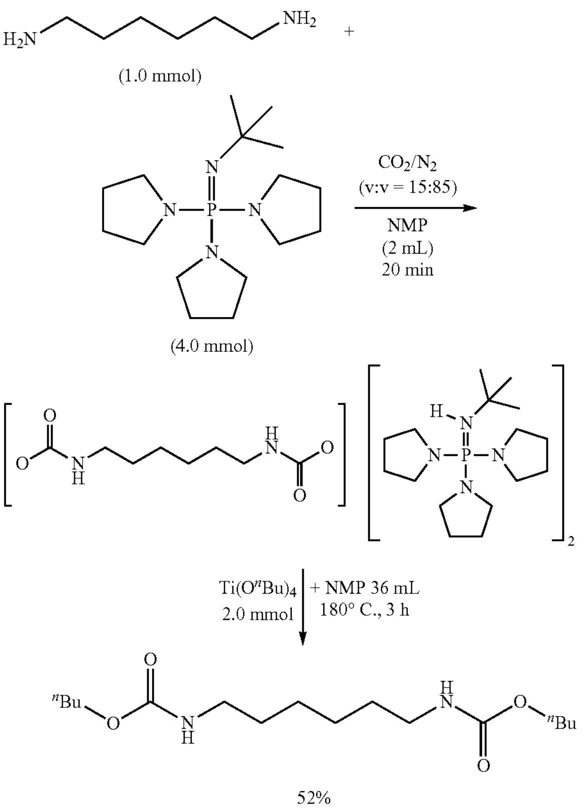

It has been indicated that a carbamic acid alkyl ester can be produced by adding titanium alkoxide as a metal alkoxide into a reaction system where a carbamic acid salt is generated from amine and carbon dioxide as raw materials, and allowing the resulting mixture to react. It has also been indicated that a carbamic acid alkyl ester can be produced by use of a low-concentration carbon dioxide gas where the volume of carbon dioxide in a carbon dioxide-containing mixed gas is 15%.

Examples of the Third Aspect of the Present Invention

Synthesis Example 1: Synthesis of Benzylammonium N-benzylcarbamate

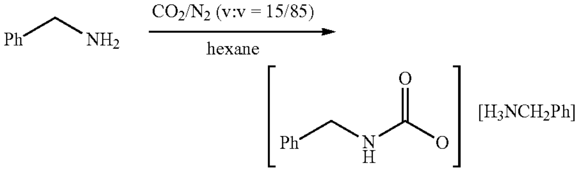

Benzylamine (40 g, 2.0 mmol) and hexane (1 L) were added into a reaction vessel, and a carbon dioxide/nitrogen mixed gas (1 atm, v:v=15:85) was allowed to pass at a flow rate of 0.5 L/min for 3 hours. After completion of the reaction, a white precipitate generated was separated by filtration, washed with hexane and thereafter dried in vacuum, and thus benzylammonium N-benzylcarbamate was obtained at a yield of 93%.

Synthesis Example 2: synthesis of N-(2-ammonioethyl)carbamate

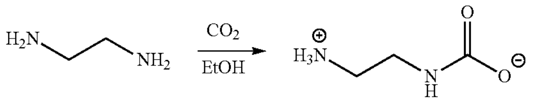

Ethylenediamine (3.0 g, 49.9 mmol) and ethanol (30 mL) were added into a reaction vessel, and a carbon dioxide gas (1 atm) was allowed to pass at a flow rate of 0.3 L/min for 5 minutes. After completion of the reaction, a white precipitate generated was separated by filtration, washed with ethanol and thereafter dried in vacuum, and thus N-(2-ammonioethyl)carbamate was obtained at a yield of 93%.

Example 5-1

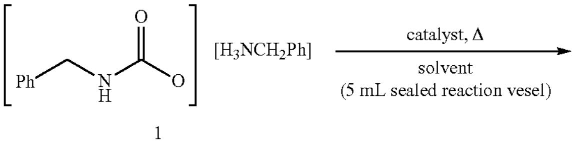

1

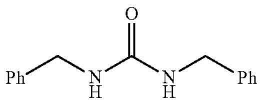

2

Benzylammonium N-benzylcarbamate (608 mg, 2.34 mmol) obtained in Synthesis Example 1, dibutyltin oxide (100 mg, 0.4 mmol), and acetonitrile (4.3 mL) were added into a sealed reaction vessel having a volume of 5 mL, and reacted at 180° C. for 1 hour. After completion of the reaction, the solvent was removed by an evaporator, and purification was performed by a silica gel column using a dichloromethane/methanol mixed solvent (v:v=98/2). The solvent was removed by the evaporator, recrystallization was performed with dichloromethane and hexane, and thus N,N'-dibenzylurea was obtained at a yield of 47%. As shown in the Table, the yield of N,N'-dibenzylurea before purification was 54%. The yield was determined with mesitylene (50 mg) as an internal standard according to $^1H$ NMR.

Examples 5-2 and 5-3

Each N,N'-dibenzylurea was obtained in the same manner as in Example 5-1 except that the reaction time was changed as shown in Table 4. The yields are shown in Table 4.

Example 5-4

N,N'-dibenzylurea was obtained in the same manner as in Example 5-1 except that the amount of use of dibutyltin oxide was changed as shown in Table 4. The yield is shown in Table 4.

Example 5-5

N,N'-dibenzylurea was obtained in the same manner as in Example 5-1 except that the solvent was changed as shown in Table 4. The yield is shown in Table 4.

Example 5-6

N,N'-dibenzylurea was obtained in the same manner as in Example 5-1 except that no solvent was used. The yield is shown in Table 4.

Example 5-7

N,N'-dibenzylurea was obtained in the same manner as in Example 5-1 except that the solvent was changed as shown in Table 4. The yield is shown in Table 4.

Example 5-8

Benzylammonium N-benzylcarbamate (517 mg, 2.00 mmol) obtained in Synthesis Example 1, dibutyltin oxide (50 mg, 0.20 mmol), and 1,3-dimethyl-2-imidazolidinone (DMI (registered trademark)) (4.5 mL) were added into a sealed reaction vessel having a volume of 5 mL, and reacted at 170° C. for 15 hours. After completion of the reaction, the yield of N,N'-dibenzylurea was 59%. The yield was determined with mesitylene (50 mg) as an internal standard according to $^1H$ NMR.

Examples 5-9 to 5-14

Each N,N'-dibenzylurea was obtained in the same manner as in Example 5-1 except that the catalyst was changed as shown in Table 4. The yield is shown in Table 4.

Example 5-15

N,N'-dibenzylurea was obtained in the same manner as in Example 5-8 except that the catalyst was changed as shown in Table 4. The yield is shown in Table 4.

TABLE 4

| Example No. | 1 (mmol) | Catalyst | (mmol) | Solvent | (mL) | temp. (°C) | time (h) | NMR yield of 2 (%) |
|---|---|---|---|---|---|---|---|---|
| 5-1 | 2.34 | $Bu_2SnO$ | 0.4 | MeCN | 4.3 | 180 | 1 | 54(47*) |
| 5-2 | 2.34 | $Bu_2SnO$ | 0.4 | MeCN | 4.3 | 180 | 2 | 45 |
| 5-3 | 2.34 | $Bu_2SnO$ | 0.4 | MeCN | 4.3 | 180 | 5 | 43 |
| 5-4 | 2.34 | $Bu_2SnO$ | 0.04 | MeCN | 4.3 | 180 | 1 | 3 |
| 5-5 | 2.34 | $Bu_2SnO$ | 0.4 | THF | 4.3 | 180 | 1 | 15 |
| 5-6 | 2.34 | $Bu_2SnO$ | 0.4 | — | — | 180 | 1 | 6 |
| 5-7 | 2.34 | $Bu_2SnO$ | 0.4 | MeCN(dry) | 4.3 | 180 | 1 | 43 |
| 5-8 | 2.0 | $Bu_2SnO$ | 0.2 | DMI | 4.5 | 170 | 15 | 59 |
| 5-9 | 2.34 | $Zn(OAc)_2$ | 0.4 | MeCN | 4.8 | 180 | 1 | 2 |
| 5-10 | 2.34 | $Zn(OAc)_2$ | 0.4 | MeCN | 4.3 | 180 | 1 | 7 |
| | | phen | 1.2 | | | | | |
| 5-11 | 2.34 | $Ni(OAc)_2$ | 0.4 | MeCN | 4.3 | 180 | 1 | 3 |
| 5-12 | 2.34 | $Ti(OMe)_4$ | 0.4 | MeCN | 4.3 | 180 | 1 | 52 |
| 5-13 | 2.34 | $Ti(Cp)_2(OTf)_2$ | 0.4 | MeCN | 4.3 | 180 | 1 | 55 |
| 5-14 | 2.34 | $Ti(Cp)_2Cl_2$ | 0.4 | MeCN | 4.3 | 180 | 1 | 44 |
| 5-15 | 2.0 | $Ti(Cp)_2Cl_2$ | 0.2 | DMI | 4.5 | 170 | 15 | 54 |

*Yield of isolation (silica gel column chromatography + recrystallization), phen =1,10-phenanthroline It has been found from the foregoing results that a tin-based catalyst and a titanium-based catalyst provide a urea derivative at a particularly high yield. It has also been found that a urea derivative is obtained at a particularly high yield in the case of use of acetonitrile and 1,3-dimethyl-2-imidazolidinone for a reaction solvent.

Example 5-16

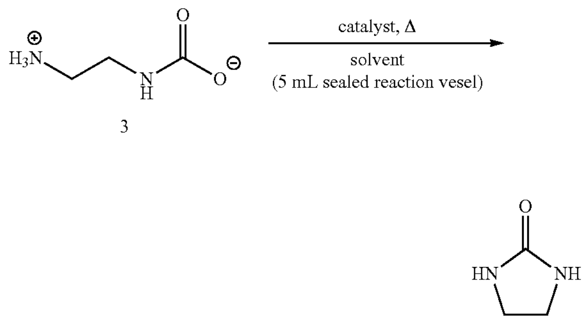

3

4

N-(2-ammonioethyl)carbamate (208 mg, 2.00 mmol) obtained in Synthesis Example 2, dibutyltin oxide (50 mg, 0.20 mmol), and 1,3-dimethyl-2-imidazolidinone (4.5 mL) were added into a sealed reaction vessel having a volume of 5 mL, and reacted at 170° C. for 15 hours. After completion of the reaction, the yield of ethylene urea was 99%. The yield was determined with mesitylene (50 mg) as an internal standard according to $^1H$ NMR. After an insoluble precipitate was removed by filtration, the solvent was distilled off under reduced pressure, the resulting solid was washed with hexane (50 mL), and thus ethylene urea was obtained as a colorless solid at a yield of 88%.

Example 5-17

Ethylene urea was obtained in the same manner as in Example 5-16 except that the solvent was changed as shown in Table 5. The yield is shown in Table 5.

Example 5-18

Ethylene urea was obtained in the same manner as in Example 5-16 except that the reaction time was changed as shown in Table 5. The yield is shown in Table 5.

Example 5-19

Ethylene urea was obtained in the same manner as in Example 5-16 except that the amount of charging was changed as shown in Table 5. The yield is shown in Table 5.

Example 5-20

Ethylene urea was obtained in the same manner as in Example 5-16 except that the catalyst and the reaction time were changed as shown in Table 5. The yield is shown in Table 5.

Example 5-21

Ethylene urea was obtained in the same manner as in Example 5-16 except that the catalyst, the solvent, and the reaction time were changed as shown in Table 5. The yield is shown in Table 5.

Example 5-22

Ethylene urea was obtained in the same manner as in Example 5-16 except that the amount of charging, the catalyst, and the reaction time were changed as shown in Table 5. The yield is shown in Table 5.

Example 5-23

Ethylene urea was obtained in the same manner as in Example 5-16 except that the catalyst and the reaction time were changed as shown in Table 5. The yield is shown in Table 5.

Example 5-24

Ethylene urea was obtained in the same manner as in Example 5-16 except that the catalyst and the reaction time were changed as shown in Table 5. The yield is shown in Table 5. DBU (registered trademark) is 1,8-diazabicyclo [5.4.0]-7-undecene.

TABLE 5

| Example No. | 1 (mmol) | Catalyst (mmol) | | Solvent (mL) | | temp. (° C.) | time (h) | NMR yield of 2 (%) |
|---|---|---|---|---|---|---|---|---|
| 5-16 | 2.0 | $Bu_2SnO$ | 0.2 | DMI | 4.5 | 170 | 15 | 99(88**) |
| 5-17 | 2.0 | $Bu_2SnO$ | 0.2 | NMP | 4.5 | 170 | 15 | 99 |
| 5-18 | 2.0 | $Bu_2SnO$ | 0.2 | DMI | 4.5 | 170 | 3 | 46 |
| 5-19 | 6.0 | $Bu_2SnO$ | 0.6 | DMI | 4.5 | 170 | 15 | 99 |
| 5-20 | 2.0 | $Ti(Cp)_2Cl_2$ | 0.2 | DMI | 4.5 | 170 | 3 | 60 |
| 5-21 | 2.0 | $Ti(Cp)_2(OTf)_2$ | 0.2 | NMP | 4.5 | 170 | 6 | 91 |
| 5-22 | 6.0 | $Hf(OTf)_4$ | 0.04 | DMI | 4.5 | 170 | 135 | 99 |
| 5-23 | 2.0 | $K_2CO_3$ | 0.2 | DMI | 4.5 | 170 | 3 | 27 |
| 5-24 | 2.0 | DBU | 0.2 | DMI | 4.5 | 170 | 3 | 45 |

**Yield of isolation (after distillation off of solvent, washing with hexane)

INDUSTRIAL APPLICABILITY

According to the first aspect of the present invention, a carbamic acid salt can be produced from carbon dioxide at a partial pressure lower than an ordinary pressure. A carbamic acid salt obtained by the production method of the first aspect of the present invention can be used for synthesizing a urea derivative and a carbamic acid ester, and the method can serve as a technique for converting a low-concentration carbon dioxide included in an exhaust gas or the like, into a useful chemical product.

According to the second aspect of the present invention, a carbamic acid ester can be produced with a carbamic acid salt and a metal alkoxide as raw materials. According to the second aspect of the present invention, a carbamic acid salt can be produced from low-concentration carbon dioxide mixed gas as a raw material and a carbamic acid ester can be produced therefrom, and therefore, a low-concentration carbon dioxide included in an exhaust gas or the like can be effectively utilized. Furthermore, the metal alkoxide used in the second aspect of the present invention can be recovered after the reaction and then reproduced with an alcohol, and thus a reaction is provided where only low-concentration carbon dioxide, an amine, and an alcohol are substantially consumed and is excellent in environmental friendliness.

According to the third aspect of the present invention, a urea derivative can be produced from a carbamic acid salt as a raw material by a catalyst reaction. According to the third aspect of the present invention, a carbamic acid salt can be produced from carbon dioxide as a raw material and a urea derivative can be produced therefrom, and therefore, carbon dioxide can be effectively utilized. According to the third aspect of the present invention, a urea derivative for use in various applications such as pharmaceutical products and industrial chemical products is provided.

The invention claimed is:

1. A method for producing a carbamic acid ester, comprising a reaction step of producing a carbamic acid ester having a structure represented by the following formula (a-1) or (a-2), from a carbamic acid salt and a metal alkoxide:

(a-1)

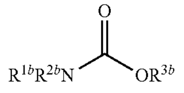

-continued (a-2)

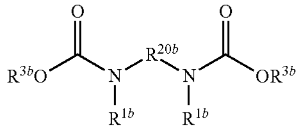

in the formulae, $R^{1b}$ each independently represents a hydrogen atom, or an unsubstituted or a substituted monovalent hydrocarbon group, $R^{2b}$ and $R^{3b}$ each independently represents an unsubstituted or a substituted monovalent hydrocarbon group, and $R^{20b}$ represents an unsubstituted or a substituted divalent hydrocarbon group.

2. The method for producing a carbamic acid ester according to claim 1, wherein the carbamic acid salt is a carbamic acid salt represented by formula (B-1), the metal alkoxide is a metal alkoxide represented by formula (C-1), and the carbamic acid ester having the structure represented by the formula (a-1) is a carbamic acid ester represented by formula (A-1):

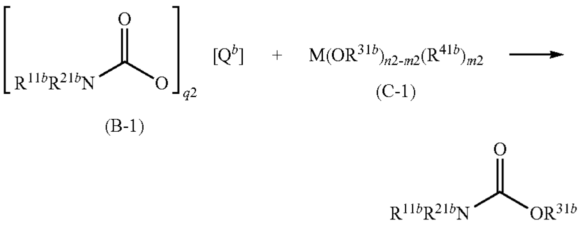

(C-1)

(B-1)

(A-1)

in the formulae, $R^{11b}$ represents a hydrogen atom, or an unsubstituted or a substituted monovalent hydrocarbon group; $R^{21b}$ and $R^{31b}$ each independently represents an unsubstituted or a substituted monovalent hydrocarbon group; $R^{41b}$ each independently represents an unsubstituted or a substituted hydrocarbon ligand, an unsubstituted or a substituted alkoxy ligands, amide ligands, and halide ligands different from $—OR^{31b}$; M represents a metal atom or a semimetal atom; n2 represents the oxidation number of M and (n2−m2) is an integer of 1 to 6; m2 represents an integer of 0 or more and (n2−1) or less; $Q^b$ represents a q2-valent counter cation; and q2 is 1 or 2.

3. The method for producing a carbamic acid ester according to claim 2, wherein $Q^b$ is a cation selected from the group consisting of an ammonium cation, an amidinium cation, a guanidinium cation, a phosphonium cation, a phosphazenium cation, a carbocation, an alkali metal cation, and an alkaline earth metal cation.

4. The method for producing a carbamic acid ester according to claim 1, wherein the carbamic acid salt is a carbamic acid salt represented by formula (B-2), the metal alkoxide is a metal alkoxide represented by formula (C-2), and the carbamic acid ester having the structure represented by the formula (a-2) is a carbamic acid ester represented by formula (A-2):

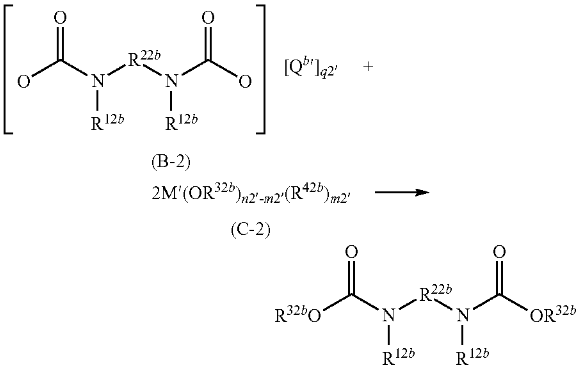

(B-2)

$2M'(OR^{32b})_{n2'-m2'}(R^{42b})_{m2'}$ (C-2)

(A-2)

in the formulae, $R^{12b}$ each independently represents a hydrogen atom, or an unsubstituted or a substituted monovalent hydrocarbon group; $R^{22b}$ represents an unsubstituted or a substituted divalent hydrocarbon group; $R^{32b}$ each independently represents an unsubstituted or a substituted monovalent hydrocarbon group; $R^{42b}$ each independently represents an unsubstituted or a substituted hydrocarbon ligand, an unsubstituted or a substituted alkoxy ligands, amide ligands, and halide ligands different from —$OR^{32b}$; M' represents a metal atom or a semimetal atom; n2' represents the oxidation number of M' and (n2'−m2') is an integer of 1 to 6; m2' represents an integer of 0 or more and (n2'−1) or less; $Q^{b'}$ represents a (2/q2')-valent counter cation; and q2' is 1 or 2.

5. The method for producing a carbamic acid ester according to claim 4, wherein $Q^{b'}$ is a cation selected from the group consisting of an ammonium cation, an amidinium cation, a guanidinium cation, a phosphonium cation, a phosphazenium cation, a carbocation, an alkali metal cation, and an alkaline earth metal cation.

6. The method for producing a carbamic acid ester according to claim 1, wherein the metal alkoxide is at least one selected from the group consisting of a titanium compound and a silicon compound.

7. The method for producing a carbamic acid ester according to claim 1, wherein the metal alkoxide is an alkoxysilane, and the reaction step is performed in the presence of a catalyst.

8. The method for producing a carbamic acid ester according to claim 7, wherein the catalyst is at least one selected from the group consisting of an organic base carboxylic acid salt, an alkali metal salt, a zinc compound, a titanium(IV) compound, and a zirconium(IV) compound.

9. The method for producing a carbamic acid ester according to claim 1, wherein the reaction step is performed in the presence of an aprotic solvent.

10. The method for producing a carbamic acid ester according to claim 1, further comprising a carbamic acid salt production step of contacting an amino group-containing organic compound with a carbon dioxide-containing mixed gas in the presence of a base in a solvent to produce the carbamic acid salt, wherein a volume of carbon dioxide in the carbon dioxide-containing mixed gas is 0.01% or more.

11. The method for producing a carbamic acid ester according to claim 1, wherein the carbamic acid salt is produced by contacting a carbon dioxide-containing mixed gas having a partial pressure of carbon dioxide of 0.001 atm or more and less than 1 atm with an amino group-containing organic compound in the presence of a base in at least one organic solvent selected from the group consisting of an organic solvent having 2 or more and 8 or less carbon atoms.

* * * * *